US011591298B2

(12) United States Patent
Amaravadi et al.

(10) Patent No.: US 11,591,298 B2
(45) Date of Patent: Feb. 28, 2023

(54) BISAMINOQUINOLINE COMPOUNDS, PHARMACEUTICAL COMPOSITIONS PREPARED THEREFROM AND THEIR USE

(71) Applicant: THE TRUSTEES OF THE UNIVERSITY OF PENNSYLVANIA, Philadelphia, PA (US)

(72) Inventors: Ravi K. Amaravadi, Media, PA (US); Jeffrey Winkler, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/285,591

(22) Filed: Feb. 26, 2019

(65) Prior Publication Data
US 2020/0071272 A1 Mar. 5, 2020

Related U.S. Application Data

(60) Continuation of application No. 16/031,387, filed on Jul. 10, 2018, now abandoned, which is a division of application No. 15/384,823, filed on Dec. 20, 2016, now Pat. No. 10,047,052, which is a continuation of application No. 14/825,477, filed on Aug. 13, 2015, now abandoned, which is a continuation of application No. 14/114,049, filed as application No. PCT/US2012/035251 on Apr. 26, 2012, now abandoned.

(60) Provisional application No. 61/480,641, filed on Apr. 29, 2011.

(51) Int. Cl.
C07D 215/46 (2006.01)
C07D 401/12 (2006.01)
C07D 401/14 (2006.01)
A61K 45/06 (2006.01)
A61K 31/4709 (2006.01)
A61P 35/00 (2006.01)
A61P 33/06 (2006.01)
A61P 29/00 (2006.01)

(52) U.S. Cl.
CPC ........ C07D 215/46 (2013.01); A61K 31/4709 (2013.01); A61K 45/06 (2013.01); A61P 29/00 (2018.01); A61P 33/06 (2018.01); A61P 35/00 (2018.01); C07D 401/12 (2013.01); C07D 401/14 (2013.01); Y02A 50/30 (2018.01)

(58) Field of Classification Search
None
See application file for complete search history.

(56) References Cited

U.S. PATENT DOCUMENTS 2,816,893 A 12/1957 Jacob et al.
5,756,517 A 5/1998 Schohe-Loop et al.
10,221,140 B2 3/2019 Amaravadi et al.
11,001,558 B2 5/2021 Amaravadi et al.
2008/0269259 A1 10/2008 Thompson et al.
2009/0275612 A1 11/2009 Higuchi et al.
2010/0267704 A1 10/2010 Yuan et al.
2014/0050696 A1 2/2014 Amaravadi et al.
2016/0168699 A1 6/2016 Amaravadi et al.
2017/0166530 A1 6/2017 Amaravadi et al.
2018/0111904 A1 4/2018 Amaravadi et al.

FOREIGN PATENT DOCUMENTS

| DE | 1169948 B | 6/1964 |
| DE | 1296635 B | 9/1969 |
| GB | 726568 | 3/1955 |
| GB | 0999237 | 7/1965 |
| WO | 9307126 A1 | 4/1993 |
| WO | 97/48705 A1 | 6/1997 |
| WO | 01/00218 A1 | 1/2001 |
| WO | 01/02218 A1 | 1/2001 |
| WO | 2004/091485 A2 | 10/2004 |
| WO | 2007/097450 A1 | 8/2007 |
| WO | 2012/149186 A2 | 11/2012 |

OTHER PUBLICATIONS

De et al. (J. Med. Chem. 41: 4918-4926, 1998).*
Zhang et al. (Biomedicine & Pharmacotherapy 62: 65-69, 2008).*
Lum JJ, et al. Autophagy in metazoans: cell survival in the land of plenty, Nat Rev Cell Biol, 2005;6:439-448.
Amaravadi RK, Thompson CB. The roles of therapy-induced autophagy and necrosis in cancer treatment, Clin Cancer Res, 2007;13:7271-7279.
Amaravadi RK, et al. Autophagy inhibition enhanced therapy-induced apoptosis in a Myc-induced model of lymphoma. J Clin Invest, 2007;117:326-336.
Degenhardt K, et al. Autophagy promotes tumor sell survival and restricts necrosis, inflammation, and tumorgenesis. Cancer Cell, 2006;10:51-64.
Amaravadi RK. Autophagy-induced tumor dormancy in ovarian cancer. J Clin Invest, 2008;118(12):3837-3841.

(Continued)

Primary Examiner — Bong-Sook Baek
(74) Attorney, Agent, or Firm — BakerHostetler

(57) ABSTRACT

The present invention relates to novel bisaminoquinoline compounds, pharmaceutical compositions comprising these novel compounds and methods for inhibiting autophagy in biological systems. Methods of treating cancer in patients in need using compounds and/or compositions according to the present invention alone or in combination with at least one additional anticancer agent represent additional aspects of the invention. Methods of treating disease states and/or conditions in which inhibition of autophagy plays a favorable treatment role including rheumatoid arthritis, malaria, antiphospholipid antibody syndrome, lupus, chronic urticaria and Sjogren's disease, with compounds according to the present invention represent additional aspects of the invention.

15 Claims, 26 Drawing Sheets

(56) References Cited

OTHER PUBLICATIONS

Carew JS, et al. Targeting autophagy augments the anticancer activity of the histone deacetylase inhibitor SAHA to overcome Bcr-Abl-mediated drug resistance. Blood. 2007;110:313-322.

Degtyarev M, et al. Akt inhibition promotes autophagy and sensitizes PTEN-null tumors to lysomotropic agents. J Cell Biol, 2008;183:101-116.

Sotelo J, et al. Adding chloroquine to conventional treatment for glioblastome multiforme: a randomized, double-blind, placebo-controlled trial. Ann Intern Med, 2006;144:337-343.

Amaravadi RK, et al. Principles and Current Strategies tor Targeting Autophagy for Cancar Treatment. Clin Cancer Res, 2011;17:654-666.

Rosenfield MR GS, et al, Pharmacokinetic analysis and pharmacodynamic evidence of autophagy inhibition in patients with newly diagnosed glioblastoma treated on a phase I trial of hydroxychloroquine in combination with adjuvant temozolomide and radiation (ABTC 0603). J Clin Oncol, 2010;28:Abstract #3086.

Vance D, et al. Polyvalency: a promising strategy for drug design. Biotechnol Bioeng, 2008;101:428-434.

Shrivastava A, et al. Designer peptides: learning from nature. Curr Pharm Des, 2009; 15:675-681.

Girault S, et al. Antiplasmodial activity and cytotoxicity of bis-, tris-, and tetraquinolines with linear or cyclic amino linkers. J Med Chem, 2001;44:1658-1665

Vennerstrom JL, et al. Bisquinolines, 2, Antimalarial N,N-bis(7-chloroquinolin-4-yl)hetroalkanediamines. J Med Chem. 1998;41:4360-4364.

Burnett JC, et al. Novel small molecule inhibitors of botulinum neurotoxin A metalloprotease activity. Biochem Biophys Res Commun, 2003;310:85-93.

Hu C, et al. A 4-aminoquinoline derivative that markedly sensitized tumor cell killing by Akt inhibitors with a minimum cytotoxicity to non-cancer cells. Eur J Med Chem, 2010;45:705-709.

Solomon VR, et al. Design and synthesis of chloroquine analogs with anti-breast cancer property. Eur J Med Chem, 2010:48:3916-3923.

Lee WW, et al. Synthesis of Mustards from Putrescine, Cadaverine, and 1,3-Diaminopropane. J Med Chem, 1963;6:567-569.

Kaschula CH, et al. Structure-activity relationships in 4-aminoquinoline antiplasmodials. The role of the group at the 7-position. J Med Chem, 2002;45:3531-3539.

Adams A, et al. Interaction of DNA-intercalating antitumor agents with adrenoceptors, Mol Pharacol, 1985;27:480-491.

Gourdie TA, et al. DNA-directed alkylating agents. 1. Structure-activity relationships for acridine-linked aniline mustards: consequences of varying the reactivity of the mustard. J Med Chem, 1990;33:1177-1186.

Bailey DM, et al. Bispyridinamines: a new class of topical antimicrobial agents as inhibitors of dental plaque. J Med Chem, 1984;27:1457-1464.

Vicker N, et al. Novel angular benzophenazines: dual topoisomerase I and topoisomerase II inhibitors as potential anticancer agents. J Med Chem, 2002;45:721-739.

Tanida I, et al. LC3 conjugation system in mammalian autophagy. Int J Biochem Cell Biol, 2004;36:2503-2518.

Pankiv S, et al. p62/SQSTM1 binds directly to Atg8/LC3 to facilitate degradation of ubiquitinated protein aggregates by autophagy, J Biol Chem, 2007;282:24131-24145.

Yang S, et al. Pancreatic cancers require autophagy for tumor growth. Genes Dev, 2011;25:717-729.

Ma X, et al. Measurements of tumor cell autophagy predict invasiveness, resistance to chemotherapy, and survival in melanoma. Clin Cancer Res, 2011:17(10):3478-3489.

Fan QW, et al. Akt and autophagy cooperate to promote survival of drug-resistant glioma. Sci Signal, 2010;3:ra81.

Saleem A, et al. Effect of dual inhibition of apoptosis and autophagy in prostate cancer. Prostate, 2012;72:1374-1381.

Cadwell K, et al. A key rote for autophagy and the autophagy gene Atg1611 in mouse and human intestinal Paneth cells. Nature, 2008:456:259-263.

Girault S. Antiplasmodial activity and cytotoxicity of bis-, tris-, and tetraquinolines with linear or cyclic amino linkers. Journal of Medicinal Chemistry. 2001;44(11):1658-1665.

Singh S. Characterization of Simian Malarial Parasite (*Plasmodium knowlesi*)-induced Putrescine Transport in Rhesus Monkey Erythrocytes. A Novel Putrescine Conjugate Arrests in Vitro Growth of Simian Malarial Parasite (*Plasmodium knowlesi*) and Cures Multidrug Resistant Murine Malaria (*Plasmodium yoeli*) Infec. Journal of Biological Chemistry, 1997;272(23):13566-13511.

Burnett JC, et al. Novel small molecule inhibitors of botulinum neurotoxin A metalloprotease activity. Biochemical and Biophysical Research Communications, Academic Press Inc, 2003;310(1):84-93.

Srivastava S, et al. Synthesis of bisquinolines and their in vitro ability to produce methemoglobin in canine hemolysate. Bioorganic & Medicinal Chemistry Letters, 1999;9(5):653-668.

Elslager EF, et al. Synthetic Amebicides. VIII. 7,7'[Iminobis(alkyleneimino) [bis[benz[c]acridines] and Congeneric 9-Aminoacridines, 12-Aminobenz[a]acridines, [2-Aminobenz[b]acridines, and 4-Aminoquinolines. Journal of Heterocyclic Chemistry, 1968;5(5):599-607.

Adams A, et al. Differences between central and peripheral rat alpha-adrenoceptors revealed using binuclear ligands. European Journal of Pharmacology, 1986;127(1):27-35.

Ferguson LR, et al. The mutagenic effects of diacridines and diquinolines in microbial systems. Mutation Research, 1990;232(2):337-343.

Vennerstrom JL. Bisquinolines. 1.,N.N-BIS(7-Chloroquinolin-4-YL)Alkanediamines with Potential Against Chloroquine-Resistant Malaria. Journal of Medicinal Chemistry, 1992;35(11):2129-2134.

Klingenstein R. et al. Similar Structure-Activity Relationships of Quinoline Derivatives for Antiprion and Antimalarial Effects. Journal of Medicinal Chemistry, 2008;49(17):5300-5308.

Ukani R, et al. Potent adjuvantic activity of CCR1-agonistic-quinoline. Bioorganic & Medicinal Chemistry Letters, 2011:22(1):293-295.

Galanakis D, et al. Bis-quinolinium cyclophanes: toward a pharmacophore model tor the blockade of apamin-sensitive SKCa channels in sympathetic neurons. Bioorganic & Medicinal Chemistry Letters, 2004;14(16):4231-4235.

Singh A. Studies on Antibacterial Agents, III. Synthesis of N, N'-Bis (4-quinolyl-, 4-quinaldinyl-, 4-quinazolinyl-, or 9-acridinyl) polymethylenediamines and Their Sulfonamides. Chemical and Phamaceutical Bulletin, 1975, 23(8):1869-1871.

Galanakis D, et al. Synthesis and Quantitative Structure-Activity Relationship of a Novel Series of Small Conductance Ca 2+ -Activated K+ Channel Blockers Related to Dequalinium, Journal of Medicinal Chemistry, 1996;39(2):359-370.

Fan HY, et al. Dual-site binding of bivalent 4-aminopyridine- and 4-aminoquinoline-based AChE inhibitors: contribution of the hydrophobic alkylene tether to monomer and dimer affinities, Bioorganic & Medicinal Chemistry, 1999;7(11):2569-2575.

Chen JQ, et al. Bis-Quinolinium Cyclophanes: 8,14-Diaza-1,7(1,4)-diquinolinacyclotetrad ecaphane (UCL 1848), a Highly Potent and Selective, Nonpeptidic Blocker of the Apamin-Sensitive Ca 2+ -Activated K+ Channel. Journal of Medicinal Chemistry, 2000;43(19):3478-3481.

Vennerstrom J, et al. Bisquinolines. 2. Antimalarial N,N-Bis(7-chloro-quinolin-4-yl) heteroalkanediamines. Antimalatrial Bisquinolines, 1998;41:4360-4364.

Matthew, et al. Nature Reviews Cancer, 2007;7:961-967.

De et al., "Structure-Activity Relationships for Antiplasmodial Activity among 7-Substituted 4-Aminoquinolines", Journal of Medicinal Chemistry, vol. 41, No. 25, 1998, pp. 4918-4926.

Aguiar, PLoS ONE, 7(5), e37259, 1-9, 2012.

Bergeron RJ, et al. Synthesis of N4-Acylated N1,N8-Big(acyl)spermidines: An Approach to the Synthesis of Siderophores. J. Org. Chem, 1980;45:1589-1592 Rerat V, et al. alphavbeta3 Integrin-targeting Arg-Gly-Asp (RGD) peptidomimetics. Bernett, J Med Chem, 2007, 50, 2127-2136.

(56) References Cited

OTHER PUBLICATIONS

Coppens, Essays BIochem, 2011, 51:127-136. (Year: 2011).
Database Registry, (Nov. 16, 1984), Database accession No. 91066-18-1, URL: STN, XP055398170.
Database Registry, (Aug. 22, 2004), Database accession No. 730910-76:-6, URL: STN, XP055398310.
Database Registry, (Aug. 27, 2004), Database accession No. 733728-23-9, URL: STN, XP055398307.
Database Registry, (Sept. 10, 2004), Database accession No. 742637-63-4, Url: Stn, XP055398292.
Database Registry, (Nov. 25, 2004), Database accession No. 788758-30-5, URL: STN, XP055398282.
Database Registry, (Aug. 16, 2005), Database accession No. 860346-93-6, URL: STN, XP055398284.
Database Registry, (Jan. 2, 2005), Database accession No. 807289-03-8, URL: STN, XP055398288 Database Registry, (Jan. 2, 2005), Database accession No. 806635-82-5, URL: STN, XP055398291.
Hermone, Chem Medical Chem, 2008, 3, 1905-1912.
Jones S, Li X. Synthesis of chiral beta-amino acid derivatives by asymmetric hydrosilylation with. an imidazole derived organocatalyst. Tetrahedron, 2012;68:5522-5532.
Kaur, K., et al., "Amino acid, dipeptide and pseudodipeptide conjugates of ring-substituted 8-aminoquinolines: synthesis and evaluation of anti-infective, β-haematin inhibition and cytotoxic activities," European Journal of Medicinal Chemistry, vol. 52, Jun. 2012, pp. 230-241.
Lu, J Biomedical Science, 2011, 18:8, 1-13.
Madapa, S., et al., "Search for new pharmacophores for antimalarial activity. Part I: synthesis and antimalarial activity of new 2-methyl-6-ureido-4-quinolinamides," European Journal of Medicinal Chemistry, vol. 17, No. 1, Jan. 2009, pp. 203-221.
Mahalingam D, et al. Combined autophagy and HDAC inhibition: A phase I safety, tolerability, phannacokinetic, and pharmacodynamic analysis of hydroxychloroquine in combination with the HDAC inhibitor vorinostat in patients with advanced solid tumors. Autophagy, 2014;10(8):1403-1414.
Margolis BJ, et al. Assembly of 4-aminoquinolines via palladium catalysis: a mild and convenient alternative to SNAr methodology. J Org Chem, 2007;72:2232-2235.
Marquez VB, et al. Binding to deoxyribonucleic acid and inhibition of ribonucleic acid polymerase by analogue of chloroquine. Journal of Medicinal Chemistry, 1974; 17(8):856-862.
McAfee Q, et al. Autophagy inhibitor Lys05 has single-agent antitumor activity and reproduces the phenotype of a genetic autophagy deficiency. Proc Nall Acad Aci USA, 2012;109:8253-8258.
Murakami N, et.al. Facilely accessible multidrug resistance modulator derived from sucrose. Bioorg Med Chem Lett, 2003;12:3267-3270.
Rangwala R, et al. Combined MTOR and autophagy inhibition: Phasel trial of hydroxychloroquine and temsirolimus in patients with advanced solid tumors and melanoma. Autophagy, 2014;10(8):1391-1402.
Rangwala R, et al. Phase I trial of hydroxychloroquine with dose-intense temozolomide in patients with advanced solid tumors and melanoma Autophagy, 2014;10(8);1369-1379.
Rebecca VW, et al. Inhibition of autophagy enhances the effects of the KT inhibitor MK-2206 when combined with paclitaxel and carboplatin in BRAF wild-type melanoma. Pigment Cell Melanoma Res, 2014;27(3):465-478.
Rerat V, et al. alphavbeta3 Integrin-targeting Arg-Gly-Asp (RGD) peptidomimetics containing oligoethylene glycol (OEG) spacers. J Med Chem, 2009;52:7029-7043.
Rosenfeld MR, et al. A phase I/II trial of hydroxychloroquine in conjunction with radiation therapy and concurrent and adjuvant temozolomide in patients with newly diagnosed glioblastoma multiforme. Autophagy, 2014; 10(8):1359-1368.
Schlosser M, Cottet F. Silyl-Mediated Halogen/Halogen Displacement in Pyridines and Other Heterocycles. Eur J Org Chem, 2002:4181-4184.
Singh S. Characterization of Simian Malarial Parasite (*Plasmodium knowlesi*)-induced Putrescine Transport in Rhesus Monkey Erythrocytes. A Novel Putrescine Conjugate Arrests in Vitro Growth of Simian Malarial Parasite (*Plasmodium knowlesi*) and Cures Multidrug Resistant Murine Malaria (*Plasmodium yoeli*) Infec. Journal of Biological Chemistry, 1997;272(23):13506-13511.
Sinha BK, et al. Synthesis and Antitumor Properties of Bis(quinaldine) Derivatives. Journal of Medicinal Chemistry, 1977;20(11):1528-1531.
Thomas KD. Design, synthesis and antimicrobial activities of some newquinoline derivatives carrying 1,2,3-triazole moiety. Euro J Med Chem, 2010:3803.
Van Heerden Lezanne et al.; Synthesis and in vitro antimalarial activiy of a series of bisquinoline and bispyrrolo [1,2a]quinoxaline compounds. European Journal of Medicinal Chemistry 2012, 55, pp. 335-345.
Yin, Frontiers in Immunology, Jul. 2018, vol. 9, Article 1512, 1-11. (Year: 2018).

\* cited by examiner

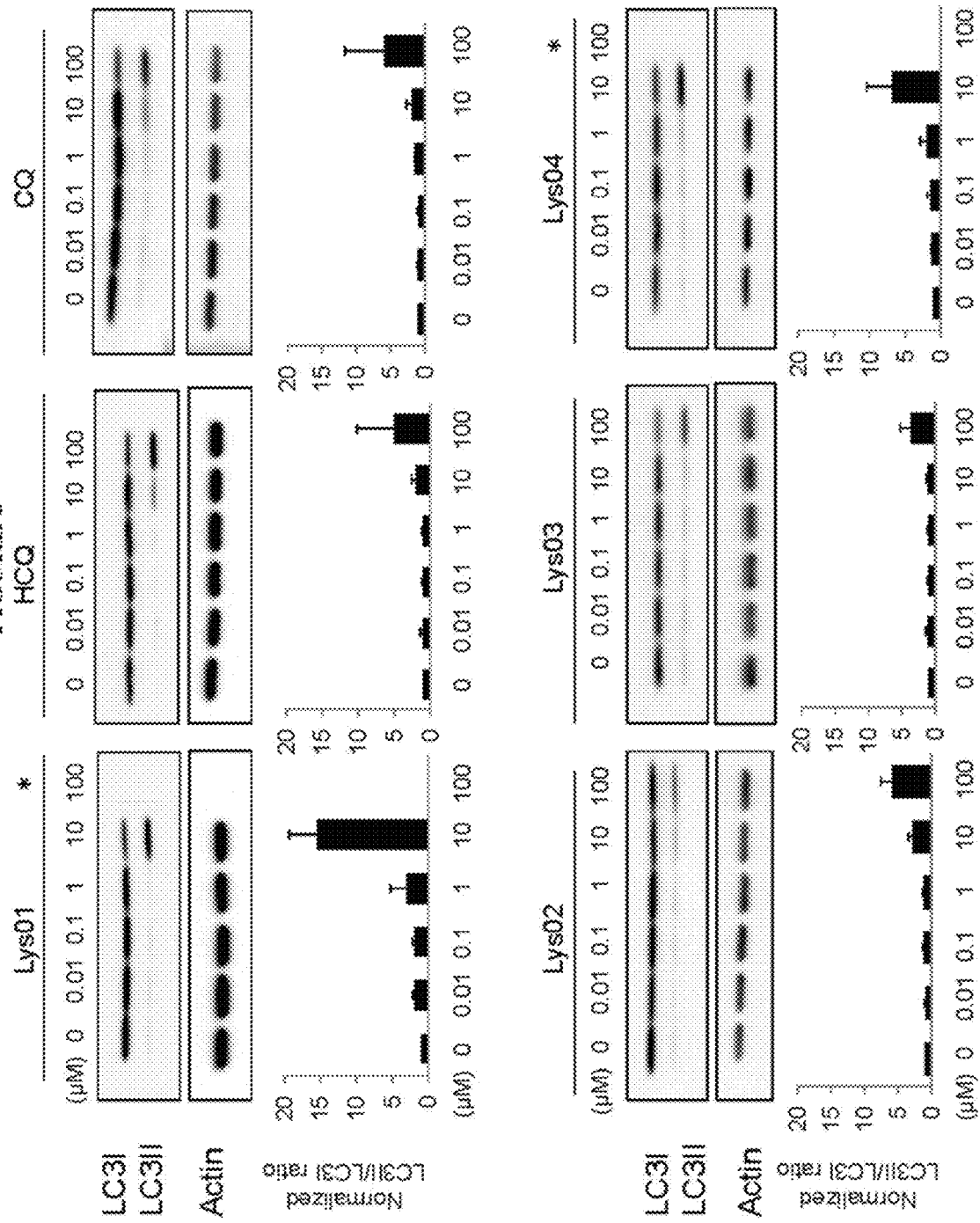

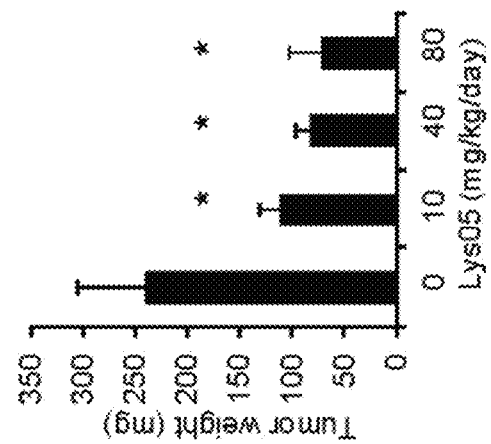
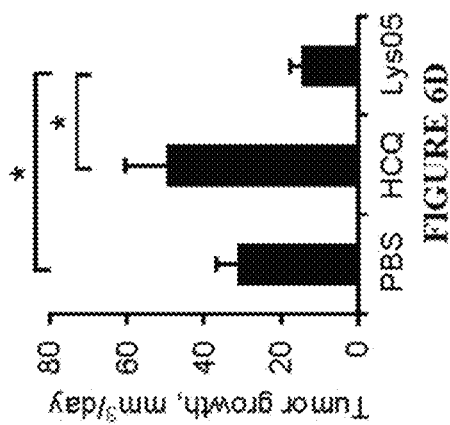
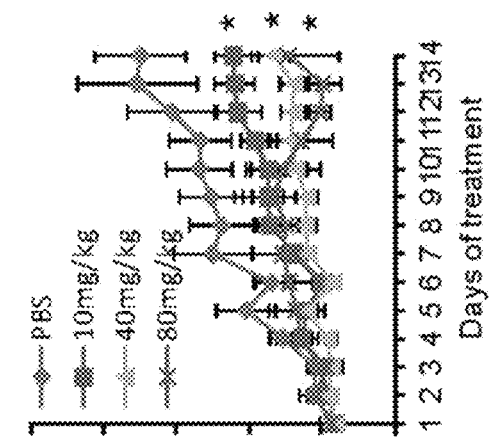
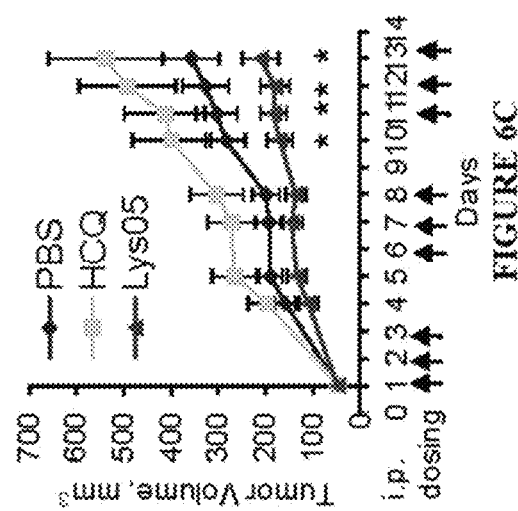
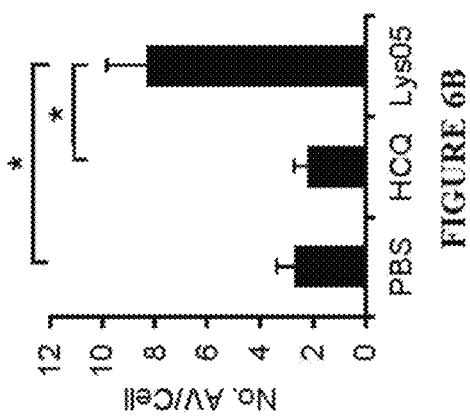
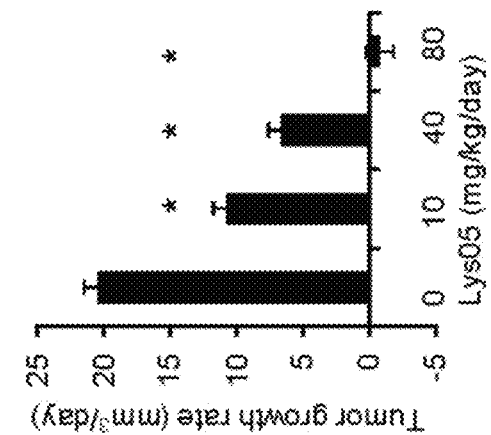

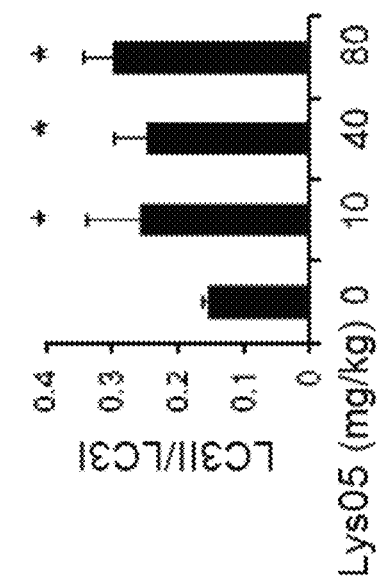
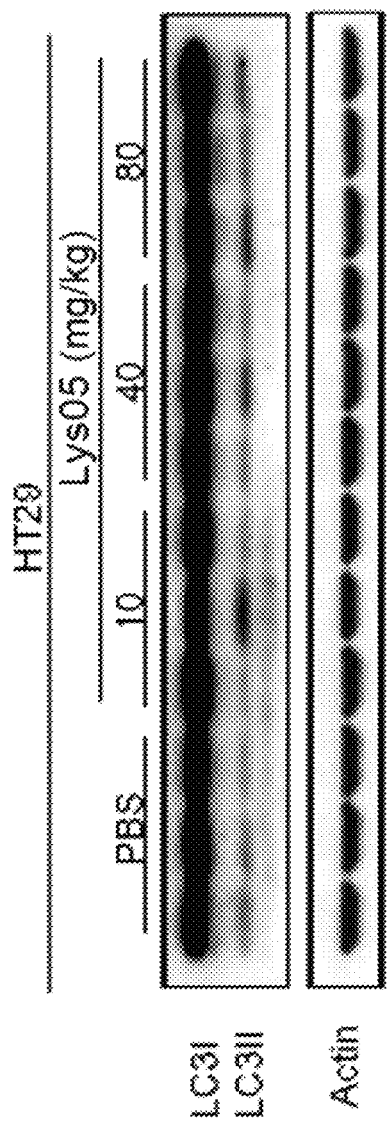
FIGURE 7C

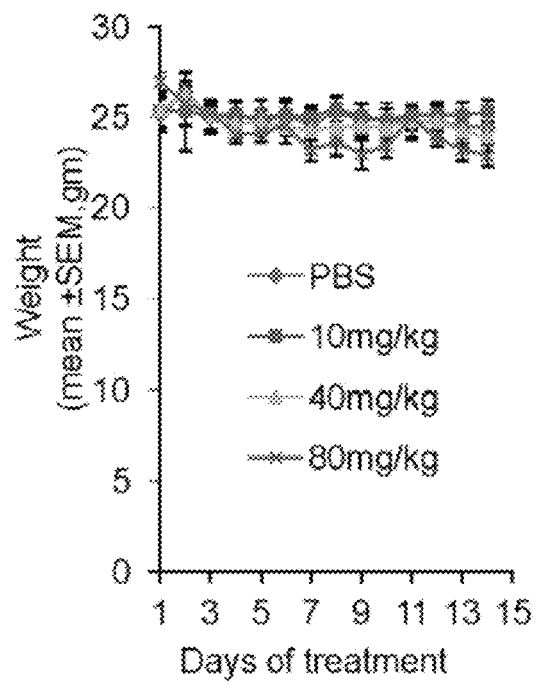
FIGURE 9A
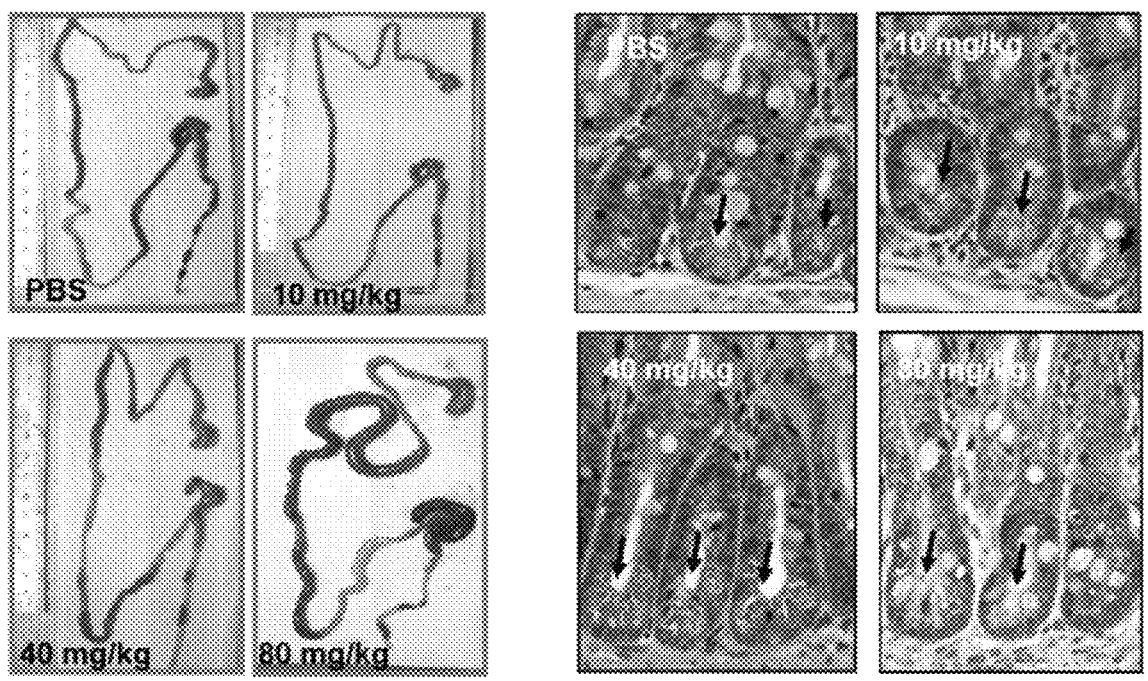
FIGURE 9B
FIGURE 9C

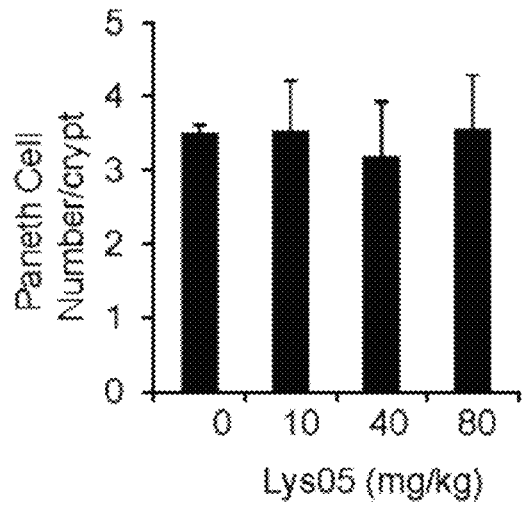
FIGURE 9D
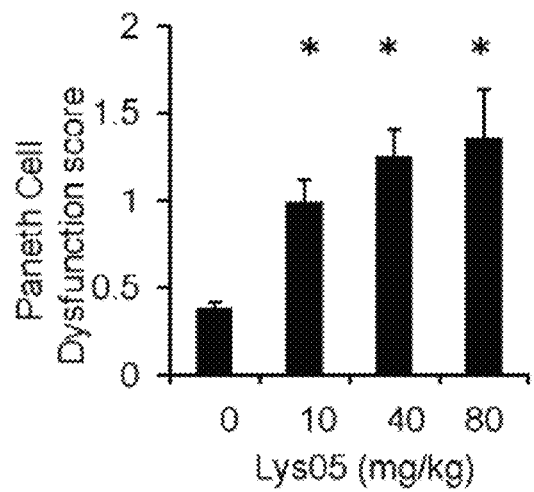
FIGURE 9E
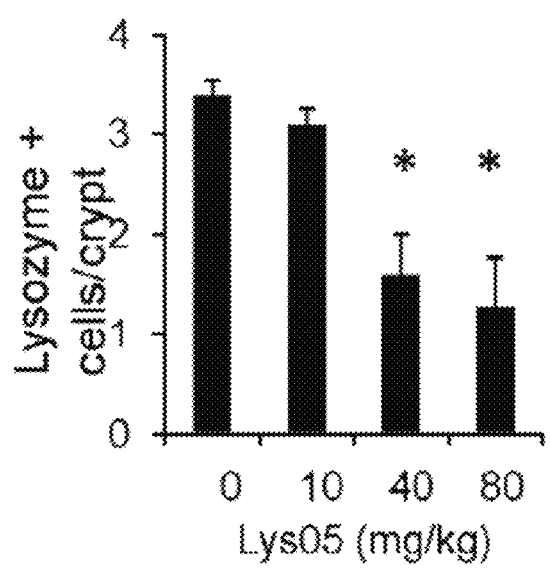
FIGURE 9F
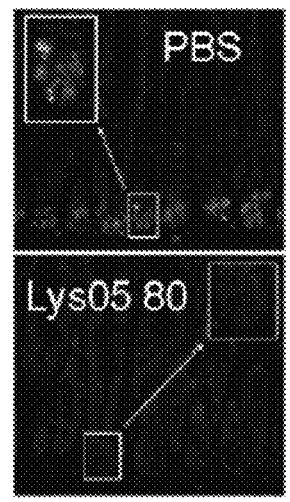

A0
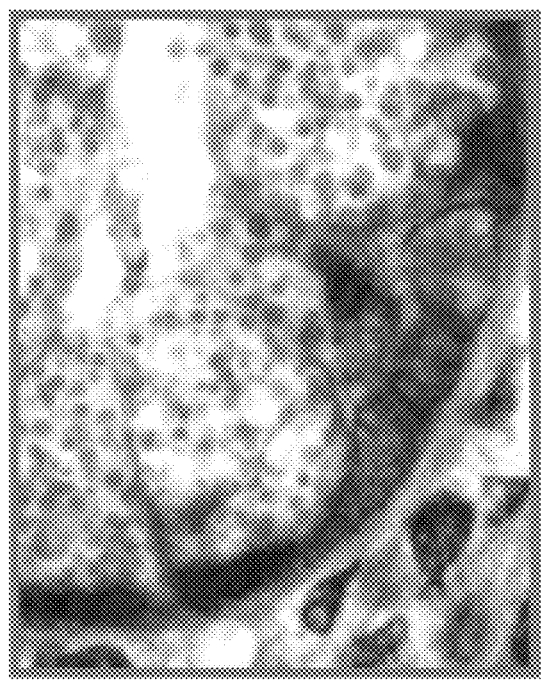
A1
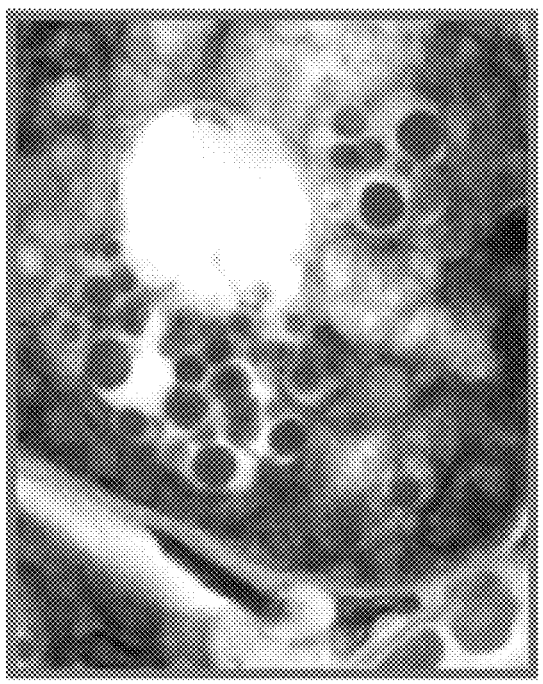
A2
A3
FIGURE 10

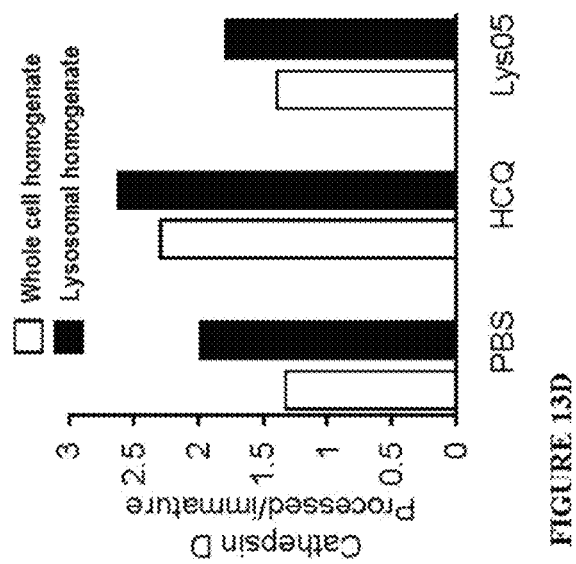
FIGURE 13D
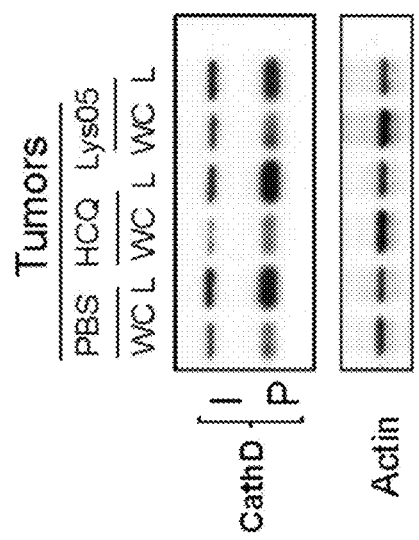
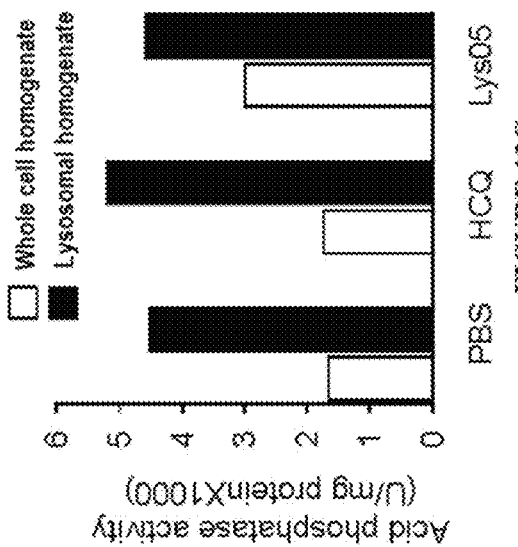
FIGURE 13C

Table 1. 72 hr MTT IC50 in LN229 cells

| Compound | IC50 (M) |
|---|---|
| Lyso12: Trifunctional | 3.19E-06 |
| Lyso1: Bifunctional | 4.60E-06 |
| Lyso11: Short ether | 5.29E-06 |
| Lyso5: Bifunctional HCL | 5.57E-06 |
| Lyso8: Trifluoro | 5.60E-06 |
| Lyso13: Central NH | 6.02E-06 |
| Lyso9: Nitro | 7.08E-06 |
| Lyso4: Long ether | 8.56E-06 |
| Lyso7: Fluoro | 1.12E-05 |
| Lyso6: Dechloro | 1.19E-05 |
| Lyso3: Methoxy | 1.67E-05 |
| CQ | 2.25E-05 |
| Lyso2: Mono + linker | 2.97E-05 |
| HCQ | 3.08E-05 |
| Lyso10: Methylketone | 1.08E-04 |

FIGURE 16

Table 2. IC50 (M) of Lyso01 derivatives in P. Falciparum

| Name | CQ-sensitive 3D7 | CQ-sensitive HB3W | CQ-resistant Dd2 | CQ-resistant 7G8 | CQ-resistant K1 |
|---|---|---|---|---|---|
| Lyso12: Trifunctional | 1.09E-07 | 1.04E-07 | 4.19E-08 | 3.87E-08 | 4.65E-08 |
| Lyso1: Bifunctional | 3.74E-09 | | 1.57E-08 | 8.10E-09 | 6.02E-09 |
| Lyso11: Short ether | 6.32E-09 | 6.44E-09 | 1.14E-08 | 3.74E-08 | 2.12E-08 |
| Lyso5: Bifunctional HCL | 4.00E-09 | | 1.11E-08 | 5.38E-09 | 4.38E-09 |
| Lyso8: Trifluoro | 2.35E-08 | 2.42E-08 | 1.93E-08 | 1.51E-08 | 2.53E-08 |
| Lyso13: Central NH | | | | | |
| Lyso9: Nitro | 4.10E-08 | 3.05E-08 | 4.70E-08 | 5.26E-08 | 4.30E-08 |
| Lyso4: Long ether | 4.39E-09 | | 1.07E-08 | 8.12E-09 | 8.66E-09 |
| Lyso7: Fluoro | 1.26E-08 | 1.24E-08 | 1.33E-08 | 3.97E-08 | 1.42E-08 |
| Lyso6: Dechloro | 8.58E-08 | 8.48E-08 | 3.60E-07 | 8.63E-07 | 1.22E-06 |
| Lyso3: Methoxy | 2.45E-07 | | 4.10E-07 | 5.18E-07 | 6.11E-07 |
| CQ | 4.60E-09 | 4.50E-09 | 2.05E-08 | 3.23E-08 | 4.09E-08 |
| Lyso2: Mono + linker | 2.84E-08 | | 1.28E-07 | 3.07E-07 | 1.48E-07 |
| Artesunate | 2.21E-08 | 1.73E-08 | 1.26E-08 | 7.19E-09 | 9.35E-09 |

FIGURE 17

BISAMINOQUINOLINE COMPOUNDS, PHARMACEUTICAL COMPOSITIONS PREPARED THEREFROM AND THEIR USE

RELATED APPLICATIONS

The present application is a continuation application of U.S. patent application Ser. No. 16/031,387 filed on Jul. 10, 2018, which is a divisional application of U.S. patent application Ser. No. 15/384,823 filed on Dec. 20, 2016, which is a continuation application of U.S. application Ser. No. 14/825,477, filed Aug. 13, 2015, now U.S. Pat. No. 10,047,052 issued on Aug. 14, 2018, which is a continuation application of U.S. national phase patent application Ser. No. 14/144,049, filed Oct. 25, 2013, now abandoned, which is based upon international patent application no. PCT/US12/35251 filed Apr. 26, 2012, which claims the benefit of priority of U.S. provisional application Ser. No. 61/480,641, filed Apr. 29, 2011, of identical title to the present application, the entire contents of which all of said applications are incorporated by reference herewith.

GRANT SUPPORT

This invention was made with government support under the Abramson Cancer Center Pilot grant awarded by the National Cancer Institute. The government has certain rights in the invention.

FIELD OF THE INVENTION

The present invention relates to novel bisaminoquinoline compounds, pharmaceutical compositions comprising these novel compounds and methods for inhibiting autophagy in biological systems. Methods of treating cancer in patients in need using compounds and/or compositions according to the present invention alone or in combination with at least one additional anticancer agent represent additional aspects of the invention. The use of radiation therapy in combination with the present compounds, alone or in combination with an additional anticancer agent as otherwise disclosed herein, represents an additional aspect of the invention. Methods of treating disease states and/or conditions in which inhibition of autophagy plays a favorable treatment role including rheumatoid arthritis, malaria, antiphospholipid antibody syndrome, lupus, chronic urticaria and Sjogren's disease, with compounds according to the present invention represent additional aspects of the invention.

BACKGROUND OF THE INVENTION

Autophagy consists of the sequestration of organelles and proteins in autophagic vesicles (AV) and degradation of this cargo through lysosomal fusion (1). Autophagy allows tumor cells to survive metabolic and therapeutic stresses (2-5). Multiple publications indicate therapy-induced autophagy is a key resistance mechanism to many anticancer agents. Chloroquine (CQ) (Compound 1, FIG. 1) derivatives block autophagy by inhibiting the lysosome (3, 6, 7). A randomized phase III trial of CQ versus placebo with carmustine and radiation in patients with glioma reported a trend towards a doubling in duration of survival in the patients treated with CQ (8). Based on these findings, clinical trials combining cancer therapies with hydroxychloroquine (HCQ; FIG. 1 Compound 2), (which is safer than CQ to dose escalate) have been launched. Preliminary results indicate these combinations have activity (9), but it is still unclear if this activity is consistently due to the addition of HCQ. High micromolar concentrations of HCQ are required to inhibit autophagy. While there is some pharmacodynamic evidence of autophagy inhibition with HCQ in cancer patients, it is inconsistent because adequate concentrations are not achieved in all patients (10). There is an unmet need to develop more potent inhibitors of autophagy. The design and synthesis of dimeric analogs of CQ, that exploit the thermodynamic advantages imparted by polyvalency (11, 12), has been a subject of intensive study for over 10 years (13-15). An early report by Vennerstrom (14) described the synthesis of heteroalkane-bridged bisquinolines as potential antimalarials, but none of the compounds had sufficient antimalarial activity to warrant further investigation. Subsequently, Sergheraert (13) reported that tetraquinolines, i.e., dimers of bisquinolines, afforded potent antimalarials, confirming the possibility that the application of the polyvalency strategy could afford increased potency, at least with respect to antimalarial activity.

More recently, Lee (16) has described the potentiation of AKT inhibitors by fluorinated quinoline analogs. Solomon (17) has reported the preparation of "repositioned" chloroquine dimers, based on the use of a piperazine connector. These results suggest that these chloroquine analogs could serve as bases for the development of a new group of effective cancer chemotherapeutics.

OBJECTS OF THE INVENTION

It is an object of the invention to provide novel compounds for inhibiting autophagy in biological systems, especially including patients or subjects in need.

It is another object of the invention to treat disease states and/or conditions in which inhibition of autophagy is beneficial to the disease states and/or conditions a patient or subject.

It is yet a further object of the invention to provide pharmaceutical compositions which may be used to inhibit autophagy, especially autophagy associated with disease states and/or conditions including cancer and its metastasis.

It is still a further object of the invention to inhibit, treat or prevent cancer, including the metastasis of cancer in patients or subjects in need utilizing compounds, compositions and/or methods which are presented herein.

It is still another object of the invention to inhibit, treat or prevent diseases in which the inhibition of autophagy provides a favorable effect, including rheumatoid arthritis, malaria, antiphospholipid antibody syndrome, lupus, chronic urticaria and Sjogren's disease, among others.

Any one or more of these and/or other objects of the invention may be readily gleaned from a description of the invention which follows.

BRIEF DESCRIPTION OF THE INVENTION

The present invention relates to compounds according to the chemical structure I

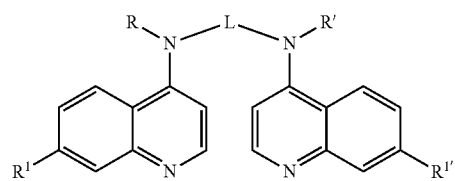

Wherein $R^1$ and $R^{1''}$ are each independently H, halo (F, Cl, Br or I), CN, $NO_2$, optionally substituted $C_1$-$C_6$ alkyl (when substituted, preferably substituted with 1 or 2 hydroxyl groups or 3-5 fluoro groups), optionally substituted O—$C_1$-$C_6$ alkyl (preferably, $OCH_3$), optionally substituted $C_2$-$C_7$ acyl (preferably acetyl) or optionally substituted $C_2$-$C_7$ ester (oxycarbonyl ester or carboxyester, preferably carboxyester);

R and R' are each independently H, a $C_1$-$C_6$ optionally substituted alkyl group, a $C_1$-$C_7$ (preferably $C_2$-$C_7$) optionally substituted acyl group, a $C_2$-$C_7$ optionally substituted carboxy ester group (which forms a urethane group with the nitrogen atom to which R or R' is bonded);

L is a

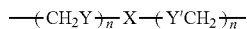

group or a

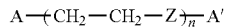

group (either A or A' may be bonded to either of the two amine groups in compound I) wherein at least one of the $CH_2$ groups in L is optionally substituted with a $C_1$-$C_3$ alkyl group which itself is optionally substituted with one or two hydroxyl groups;

X is absent, $(CH_2)_jO$, S or N—R";

Y is absent, $CH_2$, O, $CH_2O$ or N—R" and Y' is absent $CH_2$, O, $OCH_2$ or N—R", with the proviso that when one or more of X, Y and Y' is present, each of X and Y, X and Y' or Y and Y', when present, forms a stable bond;

R" is H or an optionally substituted $C_1$-$C_6$ (preferably $C_1$-$C_3$) alkyl group;

j is 1, 2 or 3 (preferably 1 or 2);

n is 0, 1, 2, 3 or 4, with the proviso that when n is 0, X is $(CH_2)_j$ where j is at least 1 and at least one $CH_2$ group is optionally substituted with a $C_1$-$C_3$ alkyl group which itself is optionally substituted with one or two hydroxyl groups;

A is absent or $(CH_2)_j$ and A' is $(CH_2)_j$ wherein at least one $CH_2$ group in A or A' is optionally substituted with a $C_1$-$C_3$ alkyl group which is itself optionally substituted with one or two hydroxyl groups;

Z is O or N—$R^Z$;

$R^Z$ is H or an optionally substituted $C_1$-$C_3$ alkyl group, or a pharmaceutically acceptable salt, enantiomer, diastereomer, solvent or polymorph thereof.

In preferred aspects of the invention, $R^1$ and $R^{1'''}$ are each independently H, a halo group, a nitro group or a trifluoromethyl group, preferably a chloro group. R and R' are preferably each independently H, a $C_1$-$C_3$ optionally substituted alkyl group itself preferably substituted with at least one hydroxyl group, an alkoxy group, an amine, monoalkyl amine or dialkyl amine group, wherein said amine group or said monoalkyl amine group is optionally substituted on the amine position with one or two 7-substituted-4-quinolinyl group(s) wherein the amine binds to the 4-position of the quinolinyl group and the 7-position of each quinolinyl group is optionally substituted, preferably with a $R^1$ and/or $R^{1'}$ group as broadly described for generic structure I above, or one or both alkyl groups of said monoalkyl amine or dialkyl amine is itself further optionally substituted with at least one hydroxyl group, an alkoxy group, an amine, a monoalkyl amine or a dialkyl amine wherein the amine or monoalkyl amine is optionally substituted on the amine position with one or two 7-substituted-quinolinyl group(s) wherein the amine binds to the 4-position of the quinolinyl group and the 7-position of each quinolinyl group is optionally substituted, preferably with $R^1$ and/or $R^{1'}$ as broadly described for generic structure I above, and each of said alkoxy groups (e.g. methoxy or ethoxy) is optionally further substituted with an alkoxy group, preferably a methoxy group, thus forming a diether substituent.

In certain preferred aspects of the invention L is a

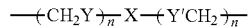

group, where X is N—R", Y and Y' are each independently absent or $CH_2$, and R" is H or a $C_1$-$C_3$ alkyl group which is optionally substituted with at least one hydroxyl group, an alkoxy group, an amine, monoalkyl amine or dialkyl amine group, wherein said amine group or said monoalkyl amine group is optionally substituted on the amine position with one or two 7-substituted-4-quinolinyl group wherein the amine binds to the 4-position of the quinolinyl group and the 7-position of each quinolinyl group is optionally substituted, preferably with $R^1$ and/or $R^{1'}$ as broadly described for generic structure I above, or one or both alkyl groups of said monoalkyl amine or dialkyl amine is itself further optionally substituted with at least one hydroxyl group, an alkoxy group, an amine, a monoalkyl amine or a dialkyl amine wherein the amine or monoalkyl amine is optionally substituted on the amine position with one or two 7-substituted-quinolinyl group(s) wherein the amine binds to the 4-position of the quinolinyl group and the 7-position of each quinolinyl group is optionally substituted, preferably with $R^1$ and/or $R^{1'}$ as broadly described for generic structure I above, and each of said alkoxy groups (e.g. methoxy or ethoxy) is optionally further substituted with an alkoxy group, preferably a methoxy group, thus forming a diether substituent.

Further preferred compounds according to the present invention include those which are presented in the various schemes which are presented in Scheme 1 and Schemes 3-10 and FIGS. 14, 15A and 15B as presented herein.

In another aspect of the invention, a pharmaceutical composition comprises a compound according to formula I above or as otherwise described herein in combination with a pharmaceutically acceptable carrier, additive or excipient, optionally in combination with at least one additional anticancer agent.

Methods of inhibiting autophagy in a biological system, in particular a patient or subject is a further aspects of this invention. In this aspect of the invention, a bisaminoquinoline compound as otherwise described herein is presented to the biological system, including administration to a patient or subject in need, in order to inhibit autophagy. The resulting inhibition may be monitored or applied in the biological system to effect a favorable result, including the inhibition, treatment and/or prevention of cancer, including metastasis of cancer, or the inhibition, treatment and/or prevention of one or more disease states or conditions in which the inhibition of autophagy provides a favorable result including rheumatoid arthritis, malaria, antiphospholipid antibody syndrome, lupus, chronic urticaria and Sjogren's disease, among others.

Methods of inhibiting, treating and/or reducing the likelihood of cancer, including metastasis of cancer and drug resistant cancer, comprises administering to a patient in need at least one compound according to the present invention, optionally in combination with at least one additional anti-cancer agent as otherwise described herein.

The present invention also relates to treating, inhibiting and/or preventing diseases, diseases states and/or conditions in a patient in need in which the inhibition of autophagy provides a favorable outcome, including rheumatoid arthritis, malaria, antiphospholipid antibody syndrome, lupus, chronic uticaria and Sjogren's disease, the method comprising administering to said patient at least one compound according to the present invention.

BRIEF DESCRIPTION OF THE FIGURES

FIG. 3. Effects of Lys01-Lys04 on LC3 immunoblotting Immunoblotting and quantification of LC3II/LC3I ratio in lysates from LN229 cells treated for 4 hours. The graphs show (mean+/−SD) LC3II/LC3I ratios of each treatment normalized to the LC3II/LC3I ratio of control treated cells for each experiment.

FIGS. 6A, 6B, 6C, 6D, 6E, 6F, 6G. In vivo autophagy inhibition and antitumor activity of Lys05. (6A) Representative electron micrographs (12,000×) of c8161 xenograft tumors harvested after 2 days of daily i.p. treatment with PBS, HCQ 60 mg/kg, or Lys05 76 mg/kg. Arrows: autophagic vesicles; scale bar 2 μm (6B) Quantification of mean+SEM number of autophagic vesicles/cell from two representative tumors from each treatment group. (C-D) 1205Lu xenografts were treated with PBS (blue), HCQ 60 mg/kg ip (green), or Lys05 76 mg/kg (red) i.p. every 3/5 days. (6C) Tumor volumes over 14 days (6D) Daily tumor growth rate. (E-G) HT29 xenografts were generated in the flanks of nude mice and treated with PBS, Lys05 10 mg/kg/ip daily, Lys05 40 mg/kg ip daily, or Lys05 80 mg/kg ip every 3/5 days. (6E) Average daily tumor growth rate. (6F) Tumor volumes over 14 days. (6G) Weight of excised tumors*p<0.05

FIGS. 7A, 7B, 7C. Autophagy inhibition and tumor necrosis in melanoma and colon cancer xenografts treated with Lys05 or HCQ. (7A) Immunoblotting against LC3 in lysates from individual c8161 tumors treated as indicated with daily i.p. injections for 48 hours. Quantification of LC3II/LC3I ration (mean=/−SEM) (7B) Tumor necrosis (arrows) in H&E stained sections of 1205Lu tumor xenografts harvested after 14 days of treatment; Electron micrographs (7000-12000λ) of melanoma tumor cells. Arrows: Autophagic vesicle (white); apoptotic cell (orange) (7C) Immunoblotting against LC3 in HT29 xenografts treated with daily dosing (10, 40 mg/kg) or 3/5 days (80 mg/kg) for 14 days.

FIGS. 9A, 9B, 9C, 9D, 9E, 9F. Lys05 treatment at the highest dose reproduces the intestinal phenotype of a genetic autophagy deficiency. (A-F) Weight and intestines were analyzed for mice bearing HT29 xenografts treated with PBS, Lys05 10-80 mg/kg. (9A) Daily weight (9B) Representative excised gastrointestinal tracts after 14 days of treatment (9C) Representative images (40×) of hemotoxylin and eosin stained ileal crypts from mice bearing HT29 xenografts (14 days), (40×) arrowsl paneth cells. (9D) Paneth cell number per crypt (9E) Paneth cell dysfunction score, * p<0.05 (9F) Scoring of lysozyme positive cells, *p+0.001. Representative images of lysosozyme immunofluorescence (green) of ileum in mice treated with PBS and Lys05 80 mg·kg IP 3/5 days.

FIG. 10. Paneth cell dysfunction scale. Under 40× power the size and number of eosinophilic granules per Paneth cell was scored for 10 Paneth cells per sample: A0=normal size and number. A1: Decreased size, normal number. A2: Normal size, decreased number. A3: decreased size and number.

FIG. 16, Table 1 provides MTT $IC_{50}$ values in LN229 for select compounds of the present invention as presented.

FIG. 17, Table 2 provides $IC_{50}$ (M) values of a number of compounds according to the present invention in *P. falciparum*.

DETAILED DESCRIPTION OF THE INVENTION

Figure 1:
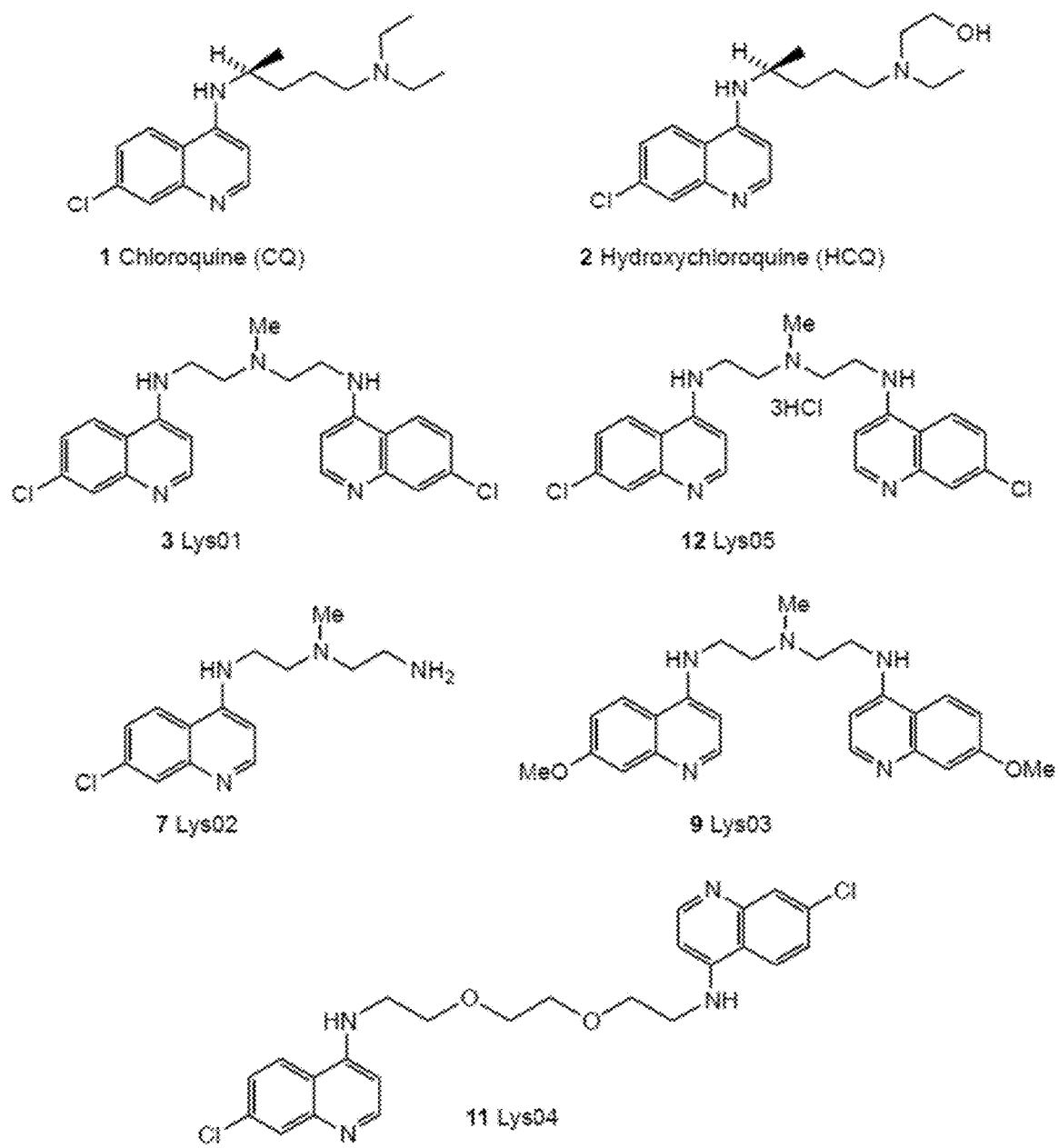
FIG. 1. Chemical structure of mono and bisaminoquinolines.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastereomers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group.

The term "bioactive agent" refers to any biologically active compound or drug which may be formulated for use in the present invention. Exemplary bioactive agents include the compounds according to the present invention which are used to inhibit autophagy and to treat cancer as well as other compounds or agents which are otherwise described herein.

The terms "treat", "treating", and "treatment", are used synonymously to refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment, principally of cancer. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, in the case of cancer.

The term "pharmaceutically acceptable" as used herein means that the compound or composition is suitable for administration to a subject to achieve the treatments described herein, without unduly deleterious side effects in light of the severity of the disease and necessity of the treatment.

The term "inhibit" as used herein refers to the partial or complete elimination of a potential effect, while inhibitors are compounds that have the ability to inhibit.

The term "prevention" when used in context shall mean "reducing the likelihood" or preventing a disease, condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients or subjects, administration with compounds according to the present invention will reduce the likelihood or inhibit a particular condition or disease state (in particular, the worsening of a disease state such as the growth or metastasis of cancer) or other accepted indicators of disease progression from occurring.

The term "autophagy" or "autophagocytosis" is used to describe a catabolic process in cells which involves the degradation of a cell's own components through lysosomes. Autophagy is a highly regulated process of biological systems that plays a normal part in cell growth development and homeostasis helping to maintain a balance between the synthesis, degradation, and subsequent recycling of cellular products. It is a major mechanism by which a cell allocates nutrients from unnecessary processes to more-essential processes.

A number of autophagic processes occur in nature, all of which have the degradation of intracellular components via the lysosome as a common feature. A well-known mechanism of autophagy involves the formation of a membrane around a targeted region of a cell, separating the contents from the rest of the cytoplasm. The resultant vesicle then fuses with a lysosome which subsequently degrades the contents.

Autophagy consists of the sequestration of organelles and proteins in autophagic vesicles (AV) and degradation of this cargo through lysosomal fusion (1). Autophagy allows tumor cells to survive metabolic and therapeutic stresses (2-5). Multiple publications indicate therapy-induced autophagy is a key resistance mechanism to many anti-cancer agents.

Diseases, disease states and/or conditions which benefit from the inhibition of autophagy include cancer (including the metastasis of cancer), rheumatoid arthritis, malaria, antiphospholipid antibody syndrome, lupus, chronic urticaria and Sjogren's disease.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of dysplasia, or loss of differentiation and orientation of cells, and have the properties of invasion and metastasis. The term cancer also within context, includes drug resistant cancers, including multiple drug resistant cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic-leukemia, lymphatic leukemia, lymphoblastic leukemia, lymnphocytic leukemia, megakaryocytic leukemia, micro- myeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. It is noted that certain epithelial tumors including ovarian, breast, colon, head and neck, medulloblastoma and B-cell lymphoma, among others are shown to exhibit increased autophagy and are principal target cancers for compounds and therapies according to the present invention.

The term "additional anti-cancer agent" is used to describe an additional compound which may be coadministered with one or more compounds of the present invention in the treatment of cancer. Such agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimiUnab, gossypol, Bio 111, 131-I-TM-601, ALT-110, BIO 140, CC 8490, cilengitide, gimatecan, L13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But) 6,Azgly 10] (pyro-Glu- His-Trp-Ser-Tyr-D-Ser(But)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, iedroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, armsacrine, anagrelide, L-asparaginase, Bacillus Calmette-Guerin (BCG) vaccine, bleomycin, buserelin, busulfan, carboplatin, cannustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, fmasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib among others.

The term "alkyl" is used herein to refer to a fully saturated monovalent radical containing carbon and hydrogen (up to 10 carbon atoms or as otherwise indicated), and which may be a straight chain, branched or cyclic. Examples of alkyl groups are methyl, ethyl, n-butyl, n-heptyl, isopropyl, 2-methyl propyl, tert-butyl, neopentyl, hexyl, heptyl, octyl, nonyl, decyl, etc.

The term "substituted" as that term relates to alkyl groups which are described above include one or more functional groups such as lower alkyl groups containing 1-6 carbon atoms which are optionally substituted with 1 or 2 hydroxyl groups or between 1 and 5 (preferably 3-5) fluoro groups, acyl ($C_1$-$C_6$), halogen (F, Cl, Br, I, e.g., alkyl halos, e.g., $CF_3$), amido, hydroxyl, carboxy/carboxylic acid, thioamido, cyano, nitro, alkenyl ($C_2$-$C_6$) alkynyl ($C_2$-$C_6$), azido, alkoxy ($C_1$-$C_6$), (including alkoxy groups which are further substituted with a $C_1$-$C_6$ alkoxy group thus producing a diether group), amino, $C_1$-$C_6$ alkylamino and dialkyl-amino, where the alkyl groups may be optionally substituted with 1 or 2 hydroxyl groups or an amine, aminoalkyl or dialkyl group which itself is substituted one or two alkyl groups or a 7-substituted-4-quinolinyl group, $C_2$-$C_6$ acylamino, $C_2$-$C_6$ oxyacylester or carboxyester, aryloxy, aryloxy($C_1$-$C_6$)alkyl, carboxamido, thio, $C_2$-$C_6$ ether or thioether, a 7-substituted-4-aminoquinolinyl group (or a substitution on an amine group which forms a 7-substituted-4-aminoqunolinyl group) and the like. Preferred substituents on alkyl groups (within context, especially on the amino group of the 7-substituted-4-aminoquinoline) or a linker which contains at least one amine group, include, for example, at least one hydroxyl group, an amine, monoalkyl amine or dialkyl amine (where one or both alkyl groups is itself further optionally substituted with a dialkyl amine or an amine substituted with one or two (preferably one) 7-substituted-4-quinolinyl group(s) where the amine group is bonded to the 4-position of the quinolinyl group) or an alkoxy group (e.g. methoxy or ethoxy) which may be further substituted with an alkoxy group, preferably a methoxy group, thus forming a diether substituent.

The term "aryl" refers to a substituted or unsubstituted monovalent aromatic radical having a single ring (e.g., phenyl) or multiple condensed rings (e.g., naphthyl). Other examples include heterocyclic aromatic (heteroaromatic or heteroaryl) ring groups having one or more nitrogen, oxygen, or sulfur atoms in the ring, in particular, quinoline groups, in particular, 7-substituted-amino quinoline groups, as well as other groups.

The term "substituted" as used in the term "substituted aryl, substituted aromatic, substituted heteroaryl, or substituted heteroaromatic" herein signifies that a substitution on the 7-position of 4-aminoquinoline may be present, said substituents being selected from atoms and groups, which when present enhance the activity of the compound as an inhibitor of autophagy. Examples of substituents that may be present in a substituted aromatic or heteroaromatic group include, but are not limited to, groups such as H, halo (F, Cl, Br or I), CN, $NO_2$, optionally substituted $C_1$-$C_6$ alkyl (when substituted, preferably substituted with 1 or 2 hydroxyl groups or 3-5 fluoro groups), optionally substituted O—$C_1$-$C_6$ alkyl (preferably, $OCH_3$), optionally substituted $C_2$-$C_7$ acyl (preferably acetyl) or optionally substituted $C_2$-$C_7$ ester (oxycarbonyl ester or carboxyester, preferably carboxyester). It is noted that each of the substituents disclosed herein may themselves be substituted.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention, especially where a cancer has metastasized or is at risk for metastasis.

The term "radiotherapy" or "radiation therapy" is used to describe therapy for cancer which may be used in conjunction with the present compounds. Radiation therapy uses high doses of radiation, such as X-rays, or other energy sources such as radioisotopes (gamma, beta or alpha emitters), to destroy cancer cells. The radiation damages the genetic material of the cells so that they can't grow. Although radiation damages normal cells as well as cancer cells, the normal cells can repair themselves and function, while the cancer cells cannot.

Radiation therapy may be used in combination with the presently claimed compounds, alone or in combination with additional anticancer compounds as otherwise disclosed herein, depending on the cancer to be treated. Radiotherapy therapy is most effective in treating cancers that have not spread outside the area of the original cancer, but it also may be used if the cancer has spread to nearby tissue. Radiotherapy is sometimes used after surgery to destroy any remaining cancer cells and to relieve pain from metastatic cancer.

Pharmaceutical Compositions

Compounds according to the present invention may be readily formulated into pharmaceutical compositions, useful in the inhibition of autophagy in a biological system and/or the inhibition, treatment or prevention of diseases states and/or conditions which benefit from the inhibition of autophagy including cancer (and its metastasis), rheumatoid arthritis, malaria, antiphospholipid antibody syndrome, lupus (systemic lupus erythematosus), chronic urticaria and Sjogren's disease. Pharmaceutical compositions comprise an effective amount of one or more compounds according to the present invention in combination with a pharmaceutically acceptable carrier, additive or excipient, optionally in combination with at least one additional agent, in the case of cancer, preferably an anticancer agent as otherwise described herein.

As noted above, the compounds and method of the invention may be used to inhibit autophagy as otherwise described herein, and are useful for the inhibition (including prophylaxis) and/or treatment of cancer and its metastasis, rheumatoid arthritis, malaria, antiphospholipid antibody syndrome, lupus (systemic lupus erythematosus), chronic urticaria and Sjogren's disease. The treatment of cancer or malaria are important aspects of the present invention.

In methods according to the present invention, subjects or patients in need are treated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for inhibiting autophagy in a biological system, including a patient or subject according to the present invention.

Figure 2:
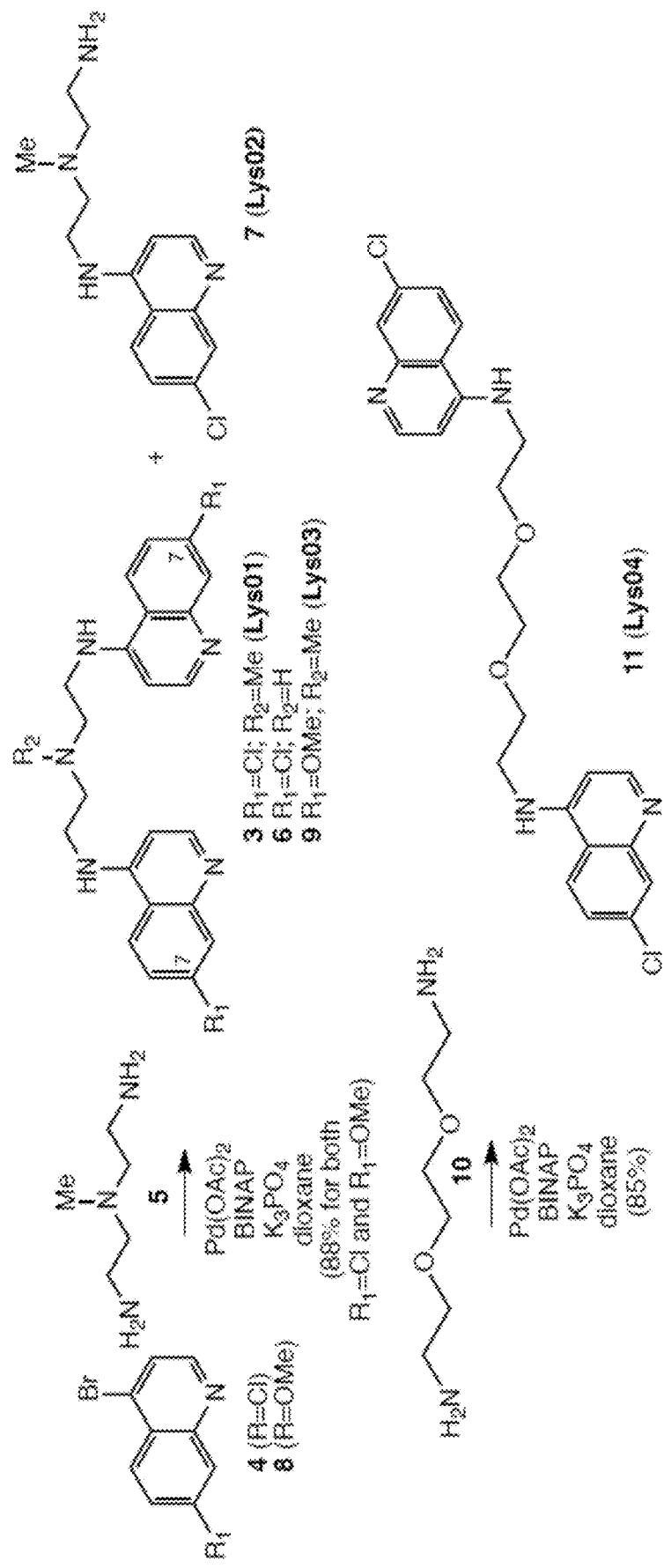
FIG. 2. Synthesis scheme for bisaminoquinolines

Synthesis of Compounds According to the Present Invention Strategy for Synthesis of Bivalent Aminoquinoline Autophagy Inhibitors The inventors have examined the application of the strategy of polyvalency (11, 12) to the synthesis of novel autophagy inhibitors by preparing a dimeric chloroquine (FIG. 1, compound 3: Lys01), from commercially available materials. Based on literature precedent (14), we envisioned the preparation of compound 3 from one equivalent of compound 5 and two equivalents of compound 6 (14), as outlined retrosynthetically in FIG. 2.

While compound 4 (R=Cl) is a known compound (14), the bisquinoline compound 3 ($R_2$=Me) has not been described in the literature. Due its putative lysosomotropism, we refer to compound 3 as Lys01. Reaction of compound 5 with two equivalents of compound 4 led to the formation of a mixture of the desired product compound 3 along with some of the monoquinoline compound 7 (FIG. 1, Lys02, FIG. 2), the synthesis of which was previously reported by Higuchi (18). To examine the role of the C-7 chlorine substituents in compound 3, we prepared compound 9 (FIG. 1, compound 9: Lys 03), the dimethoxy analog of compound 3.

To determine the importance of the polyamine connector of compound 3, we prepared the polyether analog compound 11 (FIG. 1, compound 11: Lys04) of compound 3 from the commercially available 2,2'-(ethylenedioxy)bis(ethylamine) 10 (see FIG. 2).

Figure 15A:
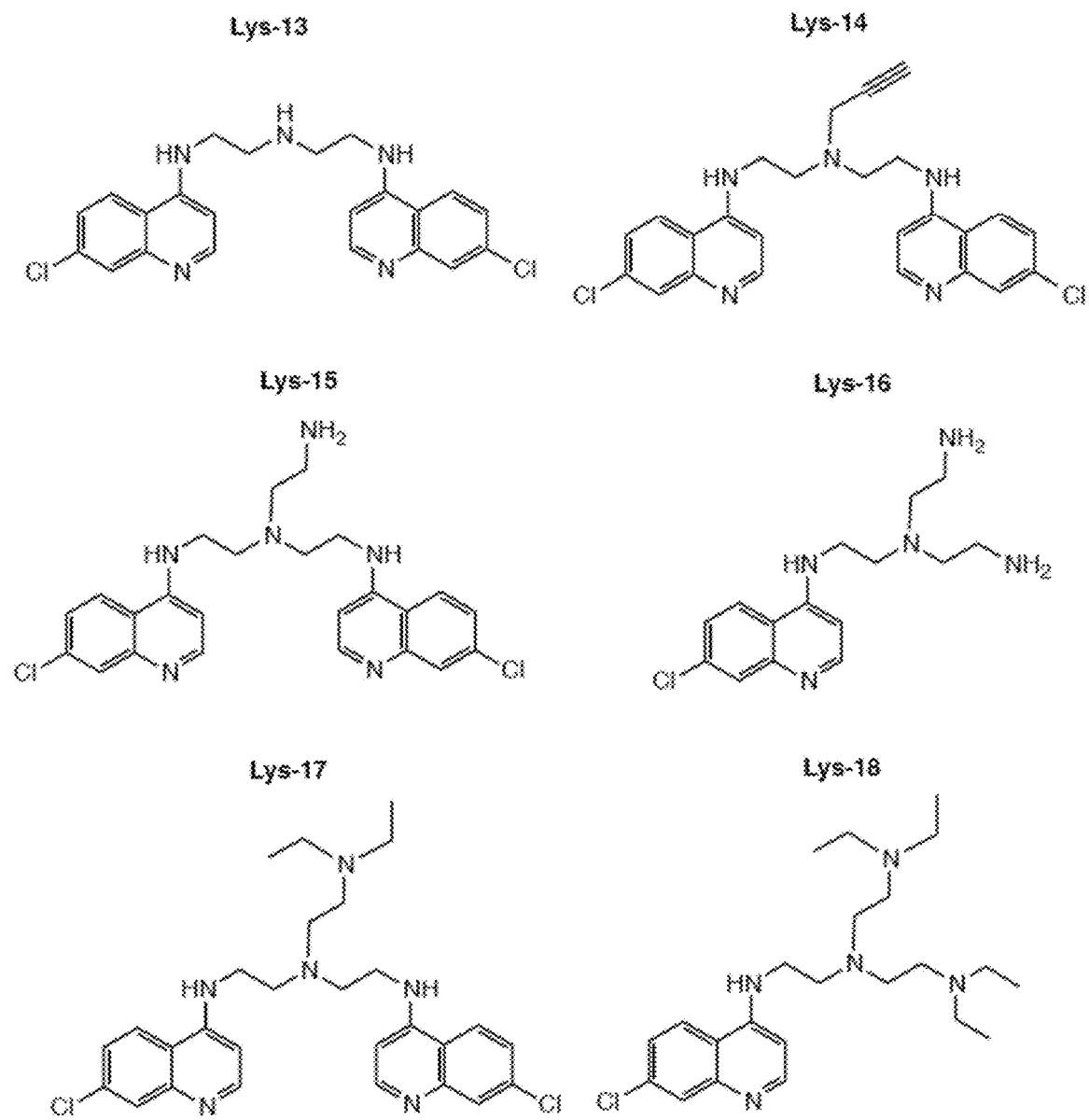
FIG. 15A. Chemical structures of synthesized compounds Lys13-Lys18; The chemical structures of Lys13-Lys18 are shown.
Figure 15B:
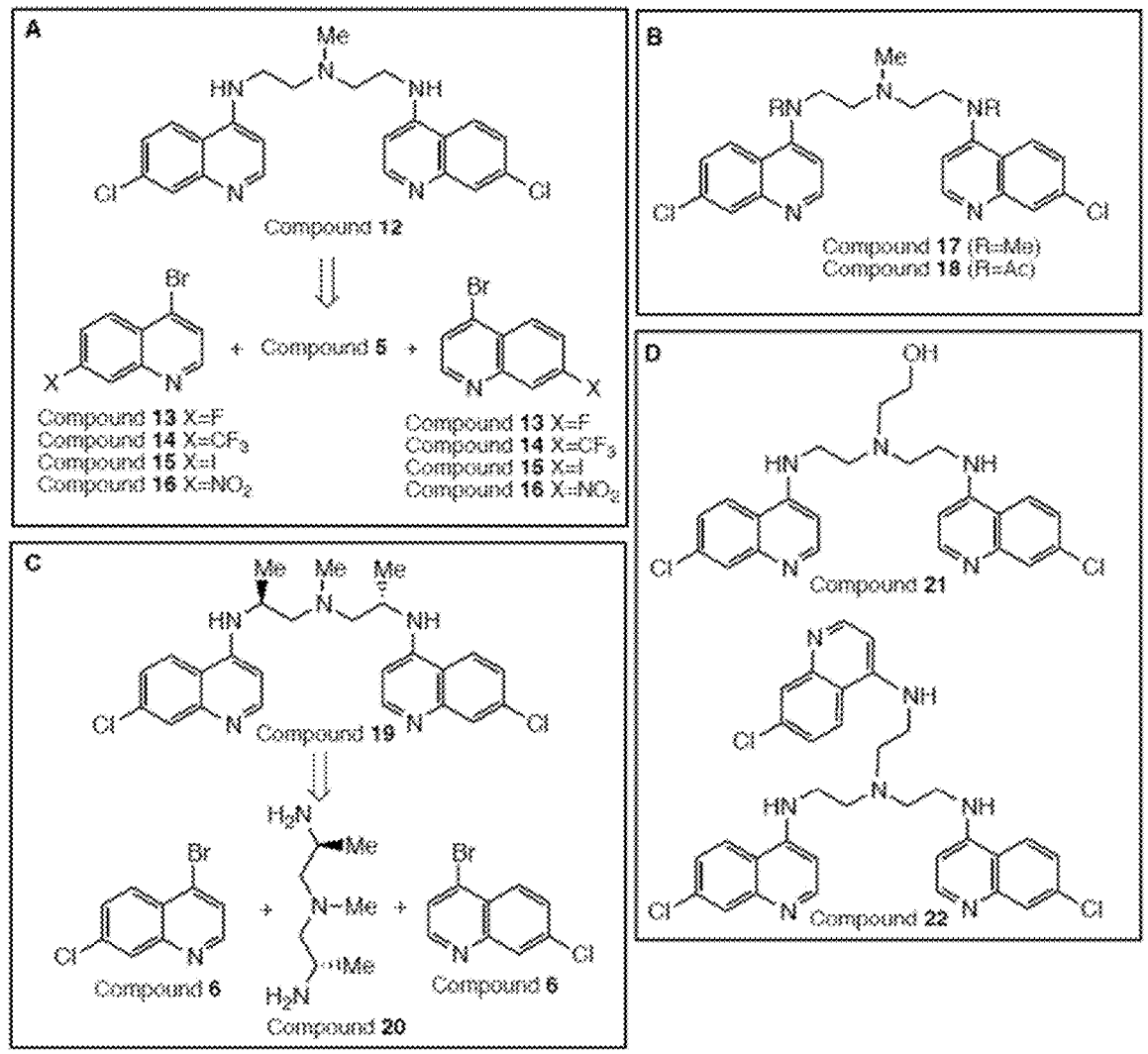
FIG. 15B shows a number of additional bisaminoquinoline autophagy inhibitors under investigation.

In an effort to obtain SAR data on the lead compound 3 (Lys01), the inventors examined the systematic modification of the structure of compound 3 (i.e., 12 R=Cl), as outlined in Scheme A of FIG. 15B. Initial efforts focused on changes in three different areas of the structure of compound 12 as examined: 1) modification of the C-7 chlorine substituent present in compound 3 (X in compound 12 of FIG. 15B); 2) modification of the C-4 nitrogen substituent, i.e., N-alkylation or acylation, as well as the adjacent carbon atom (that contains a stereocenter in CQ and HCQ (FIG. 1); and 3) modification of the N-methyl group in compound 12 (FIG. 15B).

Each of the requisite starting compounds outlined in FIG. 15B (compounds 13-16) are known or commercially available, facilitating the synthesis of a family of analogs that differ from compound 3 (12 R=Cl) by incorporating different electron-withdrawing groups, based on the work of Lee (16).

The inventors also examine the biological activity of N-alkyated and N-acylated analogs of compound 12, compound 17 and compound 18 (FIG. 15B). The preparation of these novel compounds would proceed directly from 12 (R=Cl), either by direct alkylation, reductive alkylation, or acylation.

The inventors also examine the introduction into compound 12 of the chirality that is present in CQ and HCQ (FIG. 1) as outlined in compound 19 (Scheme C of FIG. 15B). The requisite linker compound 20 could be obtained using the method of Kokotos (J. Chem. Res, Synopses 1992, 12, 391).

Finally, the modification of the structure of compound 12 via replacement of the N-methyl group (Scheme A of FIG. 15B) with other functionalities is examined. Two intriguing possibilities are shown in Scheme D of FIG. 15B, i.e., compound 21 and compound 22, in which the N-methyl group is replaced with the hydroxyethyl group present in HCQ, and in which the N-methyl group is replaced by another quinoline moiety to produce tris-quinoline compound 22. The synthetic routes for the formation of 21 and 22 are based closely on the work of Lee (19) and Solomon (17), respectively.

Scheme 1

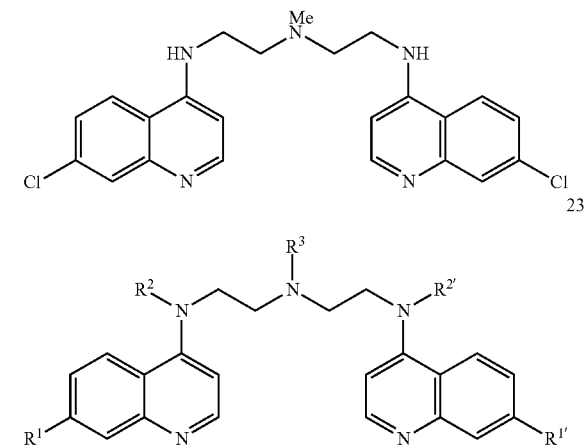

While characterization of the second generation compounds described continue, there are additional compounds which are believed to represent more potent autophagy inhibitors. Taking the lead compound as compound 12 (scheme 1; Lys01), the inventors describe more extensive systematic modification of three parts of the structure of 12, as outlined in the generic structure 23 (see above) as the next logical step in SAR analysis. Each of the three parts of the structure (R1, R2 and R3) is modified, as outlined below.

The Role of R1

The effect of substituting the chlorine moiety in chloroquine 1 (scheme 2) has been examined Scheme 2

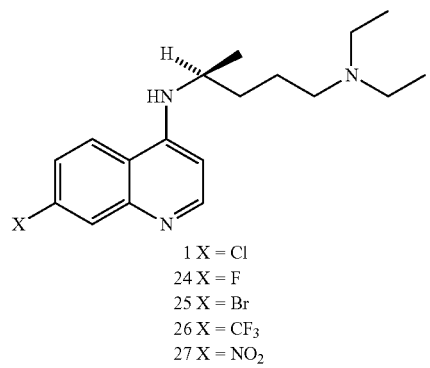

1 X = Cl
24 X = F
25 X = Br
26 X = $CF_3$
27 X = $NO_2$ by Egan and coworkers (20), who established that electron-withdrawing groups are important for the antiplasmodial activity of these 7-substituted quinolines. The inventors therefore examined these same substitutions in the case of the generic structure 23, substituting both $R^1$ and $R^{1'}$ in 23, and also examining the effect of monosubstitution, in which the R1' substituent is then either Cl as in 12 or hydrogen (X=H). The Egan study indicates that all of the requisite 4-chloro-7-substituted-quinolines are known, thereby facilitating the preparation of each of the compounds shown in Scheme 3. None of the compounds outlined in scheme 3 are known, although the synthesis of linked bis-quinolines (R1=H) has been described (21).

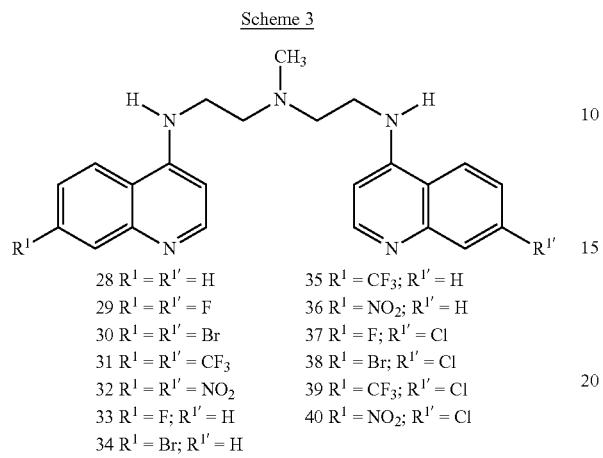

The Role of R2

The role of $R^2$=H in lead structure 3 is examined by either acetylation (R2=MeCO—; mono- or di-) or methylation (R2=Me; mono- or di-) to give the structures 41-44 shown in Scheme 4. While the homologous analogs 45 and 46 (containing one or two propylene chains between the nitrogen atoms) are known (FR 1345573; CAN 60:68181), each of the analogs 41-44 represents a novel structure.

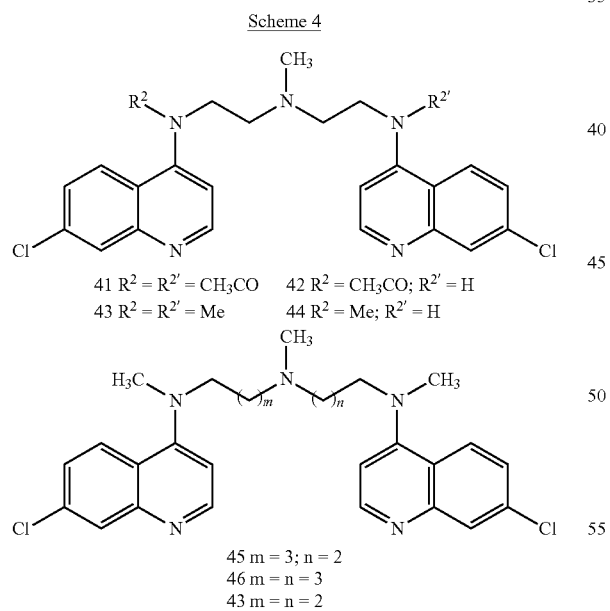

Well-tolerated substitution at $R^2$ further directs substitution of $R^2$ with a hydroxyethyl moiety, as found in hydroxychloroquine 2 (scheme 5). The reaction of anilines with ethylene oxide to give the corresponding hydroxyethyl compounds is well-precedented (22), so that conversion of the lead structure 3 to either mono- or di-hydroxyethylated analogs 47 and 48 is readily achieved.

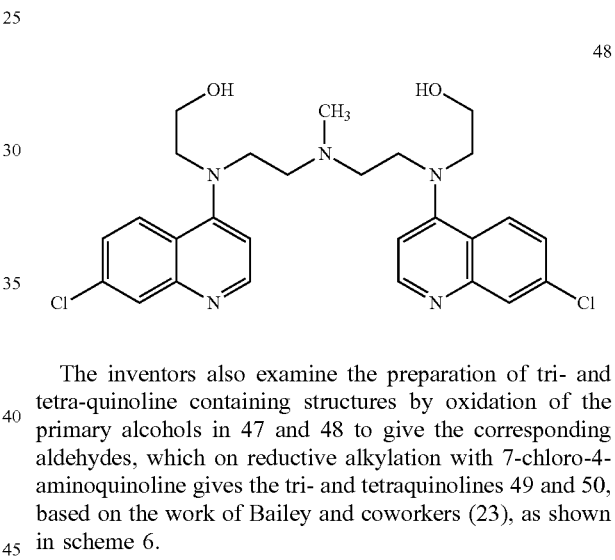

The inventors also examine the preparation of tri- and tetra-quinoline containing structures by oxidation of the primary alcohols in 47 and 48 to give the corresponding aldehydes, which on reductive alkylation with 7-chloro-4-aminoquinoline gives the tri- and tetraquinolines 49 and 50, based on the work of Bailey and coworkers (23), as shown in scheme 6.

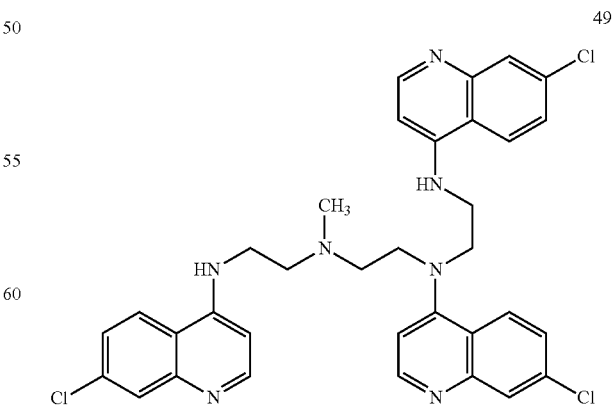

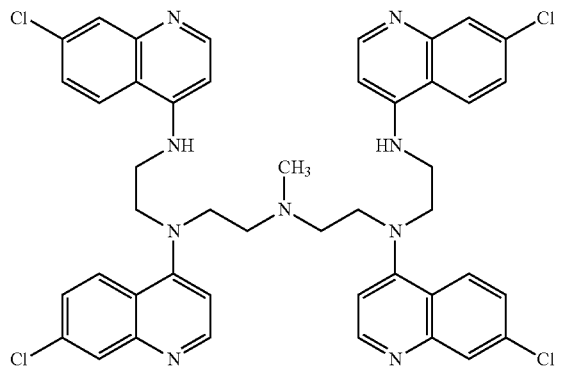

The inventors also examine the effect of incorporation of both lipophilic groups, i.e., long chain alkyl, as well as more polar substituents in the place of $R^2$ in the lead structure in Scheme 7, via alkylation of the secondary amines ($R^2$=H) with the commercially available alkylating agents 59-62, leading to the preparation of 51-58 via mono- and dialkylation of the two secondary amine functionalities, based on the work of Drefahl and Konig (Chem. Ber. 1954, 87, 1632-4).

Scheme 7

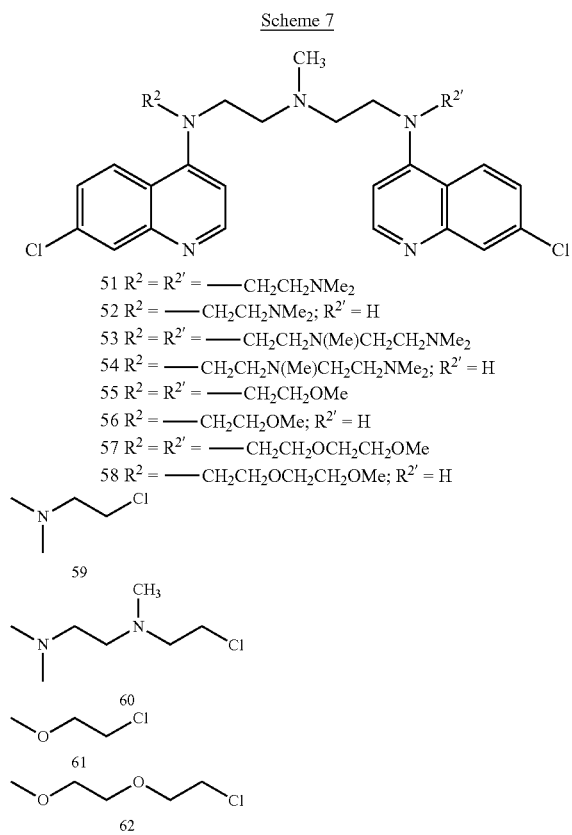

51 $R^2 = R^{2'} =$ —CH$_2$CH$_2$NMe$_2$
52 $R^2 =$ —CH$_2$CH$_2$NMe$_2$; $R^{2'} =$ H
53 $R^2 = R^{2'} =$ —CH$_2$CH$_2$N(Me)CH$_2$CH$_2$NMe$_2$
54 $R^2 =$ —CH$_2$CH$_2$N(Me)CH$_2$CH$_2$NMe$_2$; $R^{2'} =$ H
55 $R^2 = R^{2'} =$ —CH$_2$CH$_2$OMe
56 $R^2 =$ —CH$_2$CH$_2$OMe; $R^{2'} =$ H
57 $R^2 = R^{2'} =$ —CH$_2$CH$_2$OCH$_2$CH$_2$OMe
58 $R^2 =$ —CH$_2$CH$_2$OCH$_2$CH$_2$OMe; $R^{2'} =$ H

The inventors examine the effect of changing $R^3$ in the lead structure 23 (see scheme 1, above). Certain substitutions for $R^3$ are already known, such as shown in 63-65 in Scheme 8, below. The inventors prepare a series of new analogs, based on the alkylation of the known secondary amine 63 (13) with the alkylating agents shown in scheme 7 (59-62) to generate the novel structures (66-69). The substrate 70 in which $R^3$CH$_2$CH$_2$OH, i.e., the analog of 63 that corresponds most closely to hydroxychloroquine is examined. This compound is available by the same sequence used to prepare the analogs shown in Scheme 5, or by demethylation of 66.

Scheme 8

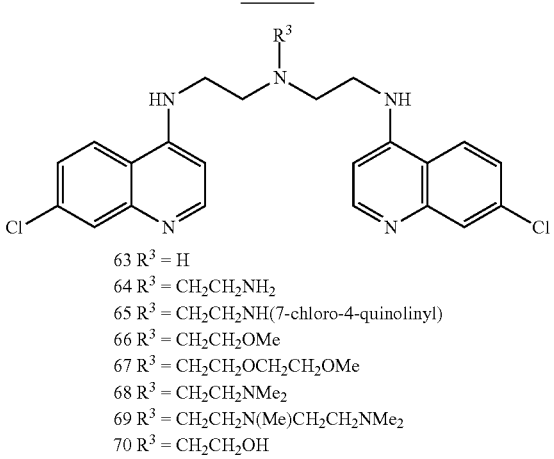

63 $R^3$ = H
64 $R^3$ = CH$_2$CH$_2$NH$_2$
65 $R^3$ = CH$_2$CH$_2$NH(7-chloro-4-quinolinyl)
66 $R^3$ = CH$_2$CH$_2$OMe
67 $R^3$ = CH$_2$CH$_2$OCH$_2$CH$_2$OMe
68 $R^3$ = CH$_2$CH$_2$NMe$_2$
69 $R^3$ = CH$_2$CH$_2$N(Me)CH$_2$CH$_2$NMe$_2$
70 $R^3$ = CH$_2$CH$_2$OH Another important difference between the lead structure 3 and chloroquine 1 (scheme 9) is the presence of the stereocenter next to the nitrogen atom in 1. The inventors also prepare hybrid structures, in which either one of both of the sides of 23 more closely resemble 1, such as 71/72 and 73/74. The requisite diamines in each case are prepared starting from (L) glutamic acid, following the procedure employed by Craig in the stereoselective synthesis of chloroquine (J. Org. Chem. 1988, 53, 1167-1170).

Scheme 9

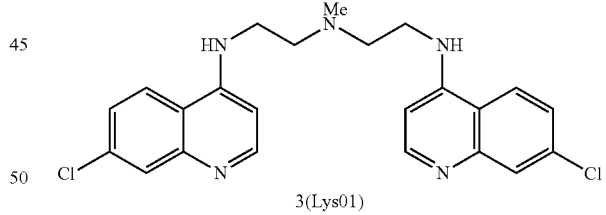

3(Lys01)

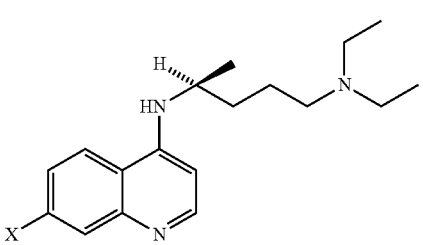

1

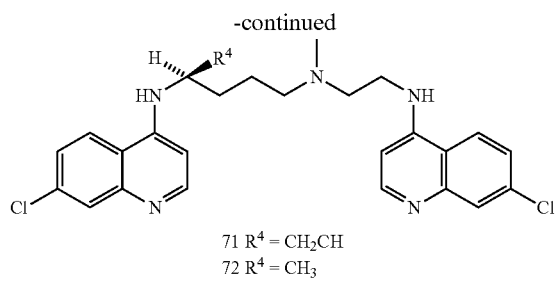

71 R⁴ = CH₂CH
72 R⁴ = CH₃

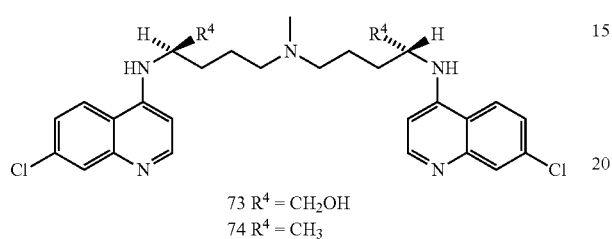

73 R⁴ = CH₂OH
74 R⁴ = CH₃

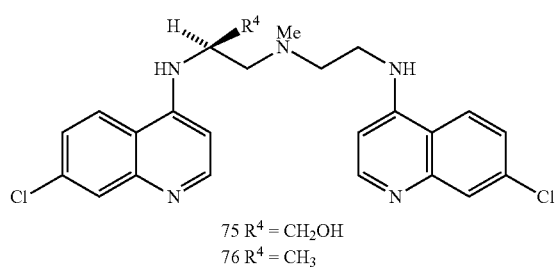

75 R⁴ = CH₂OH
76 R⁴ = CH₃

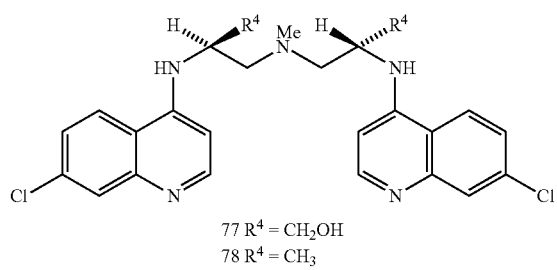

77 R⁴ = CH₂OH
78 R⁴ = CH₃

The inventors prepare the analog of the lead structure 3 containing the stereocenter present in chloroquine 1, i.e., 75/76 and 77/78, which are available from alanine and serine, respectively, using the method of Charlton and coworkers (24) via reductive alkylation.

Finally, the inventors examine a series of compounds that contain four nitrogen atoms in the tether connecting the quinoline rings, instead of the three nitrogen atoms that are present in the connector chain in 3 (scheme 9), as illustrated in scheme 10, below. Denny and coworkers (24) have described the synthesis of the requisite tetramines 81 and 82. Attachment of the additional chloroquine moieties present in 80 takes place via the same methodology employed in Scheme 8 for the synthesis of 65.

Scheme 10

79 R⁵ = Me
80 R⁵ = CH₂CH₂(7-chloro-4-quinolinyl)

81 R⁵ = Me
82 R⁵ = H

Method of Treatment According to one aspect of the invention, a method is provided for treating a mammalian patient or subject to inhibit autophagy in that patient or subject. Compounds according to the present invention described herein may be used to inhibit autophagy in a manner consistent with inhibiting, treating and/or preventing disease states and/or conditions including cancer (including metastasis of cancer), rheumatoid arthritis, malaria, antiphospholipid antibody syndrome, lupus, chronic uriticaria and Sjogren's disease.

According to the present invention, in patients or subjects in need thereof, are treated by administering to the patient or subject an effective amount of one or more compounds according to the present invention, optionally in combination with at least one additional bioactive agent useful for treating the same disease state or condition. Compounds according to the present invention may be used to inhibit, reduce the likelihood or treat cancer, including the metastasis of cancer in a patient or subject in need of such treatment. The treatment is useful for any cancer for which inhibition of autophagy represents a favorable result or for which metastasis is a risk element. Therapy with at least one additional anticancer agent as otherwise described herein is also contemplated in the present methods. The numerous cancers which may be treated pursuant to the present method are described hereinabove.

In another aspect the present invention is directed to a method for treating a disease state and/or condition which benefits from the inhibition of autophagy, including rheumatoid arthritis, malaria, antiphospholipid antibody syndrome, lupus, chronic urticaria and Sjorgen's disease. In this method, a patient or subject in need of treatment is administered an effective amount of a compound as otherwise described herein optionally in combination with a pharmaceutically acceptable carrier, additive or excipient in order to inhibit, treat and/or prevent the above disease states of conditions.

In the present invention, the method of treatment comprises administering to the subject in need of treatment, in a pharmaceutically acceptable carrier, an effective amount of a compound according to I below:

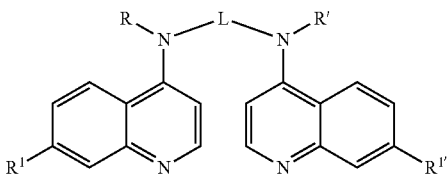

Wherein $R^1$ and $R^{1'}$ are each independently H, halo (F, Cl, Br or I), CN, $NO_2$, optionally substituted $C_1$-$C_6$ alkyl (when substituted, preferably substituted with 1 or 2 hydroxyl groups or 3-5 fluoro groups), optionally substituted O—$C_1$-$C_6$ alkyl (preferably, $OCH_3$), optionally substituted $C_2$-$C_7$ acyl (preferably acetyl) or optionally substituted $C_2$-$C_7$ ester (oxycarbonyl ester or carboxyester, preferably carboxyester);

R and R' are each independently H, a $C_1$-$C_6$ optionally substituted alkyl group, a $C_1$-$C_7$ (preferably $C_2$-$C_7$) optionally substituted acyl group, a $C_2$-$C_7$ optionally substituted carboxy ester group (which forms a urethane group with the nitrogen atom to which R or R' is bonded);

L is a

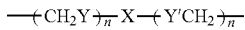

group or a

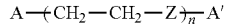

group (either A or A' may be bonded to either of the two amine groups in compound 1) wherein at least one of the $CH_2$ groups in L is optionally substituted with a $C_1$-$C_3$ alkyl group which itself is optionally substituted with one or two hydroxyl groups;

X is absent, $(CH_2)_jO$, S or N—R";
Y is absent, $CH_2$, O, $CH_2O$ or N—R" and Y' is absent $CH_2$, O, $OCH_2$ or N—R", with the proviso that when one or more of X, Y and Y' is present, each of X and Y, X and Y' or Y and Y', when present, forms a stable bond;
R" is H or an optionally substituted $C_1$-$C_6$ (preferably $C_1$-$C_3$) alkyl group;
j is 1, 2 or 3 (preferably 1 or 2);
n is 0, 1, 2, 3 or 4, with the proviso that when n is 0, X is ($CH_2$); where j is at least 1 and at least one $CH_2$ group is optionally substituted with a $C_1$-$C_3$ alkyl group which itself is optionally substituted with one or two hydroxyl groups;
A is absent or $(CH_2)_j$ and A' is $(CH_2)_j$ wherein at least one $CH_2$ group in A or A' is optionally substituted with a $C_1$-$C_3$ alkyl group which is itself optionally substituted with one or two hydroxyl groups;
Z is O or N—$R^Z$;
$R^Z$ is H or an optionally substituted $C_1$-$C_3$ alkyl group,
or a pharmaceutically acceptable salt, enantiomer, diastereomer, solvent or polymorph thereof.

In certain preferred methods of the invention, $R^1$ and $R^{1'}$ are each independently H, a halo group, a nitro group or a trifluoromethyl group, preferably a chloro group. R and R' are preferably each independently H, a $C_1$-$C_3$ optionally substituted alkyl group itself preferably substituted with at least one hydroxyl group, an amine, monoalkyl amine or dialkyl amine group, wherein said amine group or said monoalkyl amine group is optionally substituted on the amine position with a 7-substituted-4-quinolinyl group wherein the amine binds to the 4-position of the quinolinyl group, or one or both alkyl groups of said monoalkyl amine or dialkyl amine is itself further optionally substituted with at least one hydroxyl group, an amine, a monoalkyl amine or a dialkyl amine wherein the amine or monoalkyl amine is optionally substituted on the amine position with one or two 7-substituted-quinolinyl group(s) (the 7-position of each quinolinyl group may be substituted with $R^1$ and/or $R^{1'}$ as broadly described for generic structure I above), or an alkoxy group (e.g. methoxy or ethoxy) which alkoxy group may be further substituted with an alkoxy group, preferably a methoxy group (thus forming a diether substituent).

In other preferred methods of the invention L is a

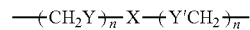

group, where X is N—R", Y and Y' are each independently absent or $CH_2$, and R" is H or a $C_1$-$C_3$ alkyl group which is optionally substituted with at least one hydroxyl group, an amine, monoalkyl amine or dialkyl amine group, wherein said amine group or said monoalkyl amine group is optionally substituted on the amine position with a 7-substituted-4-quinolinyl group wherein the amine binds to the 4-position of the quinolinyl group, or one or both alkyl groups of said monoalkyl amine or dialkyl amine is itself further optionally substituted with at least one hydroxyl group, an amine, a monoalkyl amine or a dialkyl amine wherein the amine or monoalkyl amine is optionally substituted on the amine position with one or two 7-substituted-quinolinyl group(s) (the 7-position of each quinolinyl group may be substituted with $R^1$ and/or $R^{1'}$ as broadly described for generic structure I above), or an alkoxy group (e.g. methoxy or ethoxy) which alkoxy group may be further substituted with an alkoxy group, preferably a methoxy group (thus forming a diether substituent).

Figure 14:
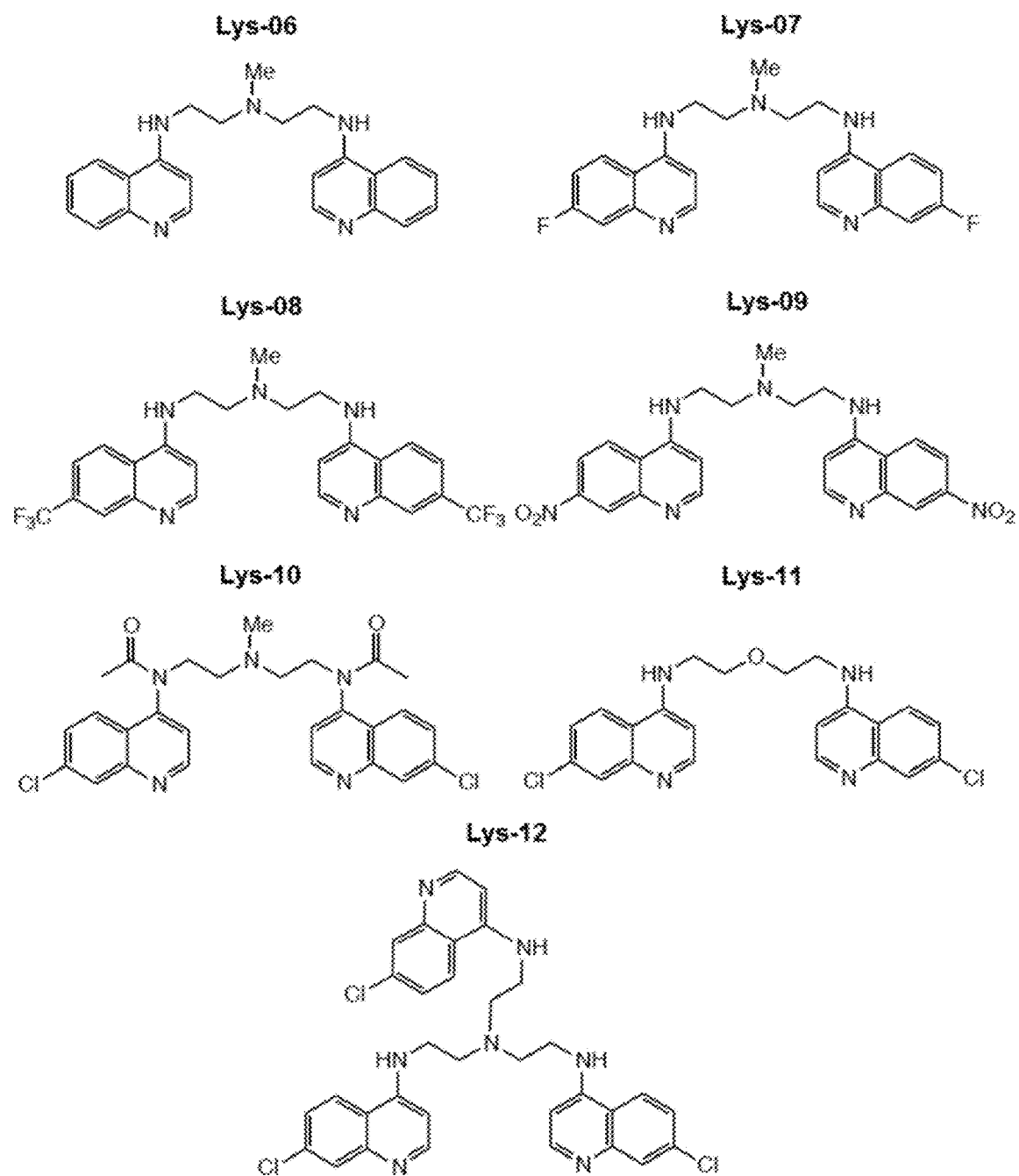
FIG. 14. Chemical structures of synthesized compounds Lys06-Lys12; The chemical structures of Lys06-Lys12 are shown.

Further preferred methods relate to the use/administration of the compounds according to the present invention which are presented in the various schemes which are presented in Scheme 1 and Schemes 3-10 and FIGS. 14, 15A and 15B as presented herein.

In the methods treating or inhibiting cancer or the metastasis of cancer, the compounds described above may be coadministered with at least one additional anticancer agent including, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimunmab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Tip-Ser-Tyr-D-Ser(But)-Leu-Arg-Pro-Azgly-$NH_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgunomab tiuxetan, androgens, decitabine, hexamethylmelamine, bexarotene, tositumomab, arsenic trioxide, cortisone, editronate, mitotane, cyclosporine, liposomal daunonlbicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others, and mixtures thereof.

In methods involving infections, disease states and/or conditions caused by rheumatoid arthritis, malaria, antiphospholipid antibody syndrome, lupus, chronic urticaria and Sjogren's disease, the compounds according to the present invention may be coadministered with additional agents which are traditionally used in therapy for these disease states and/or conditions.

EXAMPLES

The following examples illustrate and describe the present invention but are not intended to limit the invention in any way.

Synthesis of Compound 3 (Lys01).

A round-bottom flask was charged with the 4-bromo-7-chloroquinoline (compound 5) (734 mg, 3.0 mmol), Pd(OAc)$_2$ (23 mg, 0.1 mmol), BINAP (125 mg, 0.2 mmol), K$_3$PO$_4$ (1.06 g, 5.0 mmol), and triamine (compound 6) (117 mg, 1.0 mmol). Dioxane (10 mL) was introduced through the septum. The resulting suspension was stirred under argon at 90° C. for 18 h and cooled. The mixture was adsorbed onto silica gel and purified by flash chromatography (CH$_2$Cl$_2$/MeOH: 90/9/1) to afford compound 3 (387 mg, 88%) as a yellow solid. mp 199-200° C.; R$_f$=0.28 (silica gel, CH$_2$Cl$_2$/MeOH/NH$_4$OH: 90/9/1)): $^1$H NMR (500 MHz, CDCl3: δ 8.53 (d, J=5.5 Hz, 2H), 7.94 (d, J=2.0 Hz, 2H), 7.41 (d, J=9.0 Hz, 2H), 6.98 (dd, J=9.0, 2.0 Hz, 2H), 6.39 (d, J=5.0 Hz, 2H), 5.44 (s, 2H). 3.42 (q, J=5.0 Hz, 4H), 2.90 (t, J=6.0 Hz, 2H), 2.46 (s, 9H). $^{13}$C NMR (125 MHz, CDCl3): δ 152.1, 149.5, 149.1, 135.1, 128.9, 125.5, 120.6, 117.1, 99.3, 55.5, 42.4, 40.3 FTIR (thin film): 3215, 2917, 1609, 1579, 1449. HRMS-ESI (m/z): calcd for C$_{23}$H$_{24}$N$_5$Cl$_2$ [M+H]: 440.1409, found: 440.1406.

Synthesis of Compound 11 (Lys 05).

To generate a water soluble salt of compound 3, a suspension of compound 3 (896 mg, 2.04 mmol) in MeOH (40 mL) was bubbled with HCl gas for 10 min at 0° C. The mixture was stirred for another 12 h at room temperature. The solvent was removed by rotary evaporation and the residue was dried under vacuum at 50° C. overnight to afford the salt 3 (1.13 g, 100%) as a yellow solid. mp 270° C. (decomp.); $^1$H NMR (500 MHz, D$_2$O): δ 8.12 (d, J=7.0 Hz, 2H), 7.73 (d, J=9.0 Hz, 2H), 7.58 (d, J=2.0 Hz, 2H), 7.26 (dd, J=9.0, 2.0 Hz, 2H), 6.62 (d, J=2.0 Hz, 2H), 3.89 (br, 4H), 3.68 (br, 4H), 3.12 (s, 3H). $^{13}$C NMR (125 MHz, D$_2$O): δ 155.8, 142.8, 140.2, 137.2, 128.1, 123.8, 119.1, 114.8, 98.7, 52.9, 42.7, 38.2. FTIR (thin film): 3376, 3019, 2914, 1631, 1612, 1215 cm$^{-1}$. HRMS-ESI (m/z): calcd for C$_{23}$H$_{24}$N$_5$Cl$_2$ [M-3HCl+H]$^+$: 440.1409, found: 440.1408.

Biological Testing

Lys01 is a More Potent Autophagy Inhibitor than HCQ or CQ.

Figure 4A:
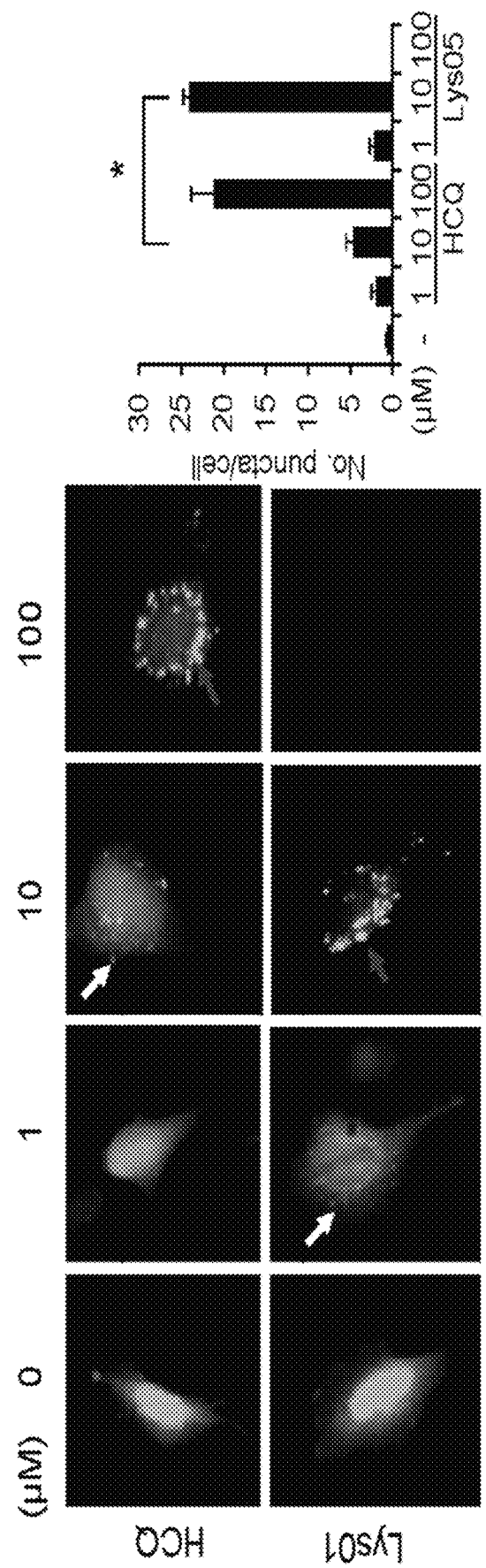
FIGS. 4A, 4B, 4C, 4D. Autophagy inhibition and cytotoxicity of Lys01 compared to HCQ (4A) Representative images of LN229 GFP-LC3 cells treated as indicated for 4 hours. White arrows: small puncta; red arrows: dense puncta. Graphs show mean+/−SEM puncta/cell. (4B) Representative electron micrographs of LN229-GFP-LC3 cells treated (4 hours) with DMSO, HCQ 10 μM, or Lys01 10 μM Arrows: Autophagic vesicles. (4C) LC3 immunoblotting of LN229 cells treated for 24 hours an indicated; calculated ratio of LC3II/LC3I ratios for bafilomycin versus control co-treatment. Above the dashed line indicates an autophagy inducer or control, below the dashed line indicated an autophagy inhibitor. (4D) MTT assay (72 hours) for 4 cell lines. Red: Lys01, Blue: Lys02, Purple: Lys03 Green: Lys04 Orange: HCQ. Values presented are means+/−SEM with 5 replicates per treatment.
Figure 4B:
Figure 4C:
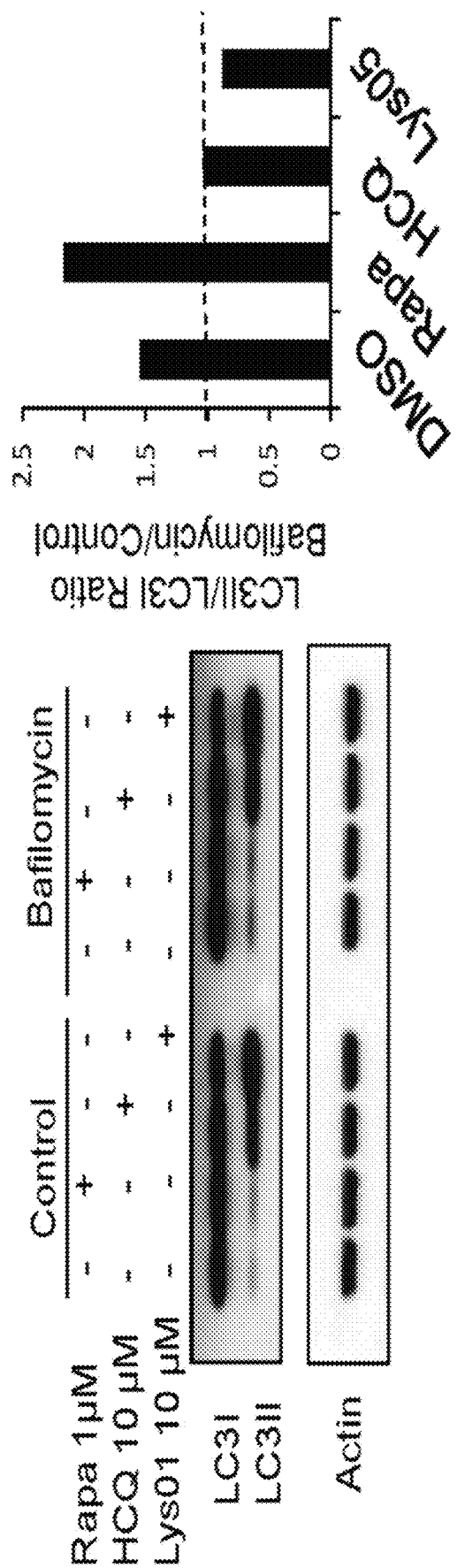

LN229 (human glioblastoma) were treated with Lys01 and derivatives Lys02, Lys03, Lys04, HCQ and CQ. Near complete cell death of cultured cells was observed in cells treated with Lys01 at concentrations of 10 μM or higher between 4-24 hours. LC3 is a ubiquitin-like protein which exists as an unconjugated form (LC3I) or conjugated to AV membranes (LC3II) (25). The ratio of LC3II/LC3I reflects the accumulation of AV in cells, and therefore effective autophagy inhibition. LC3 immunoblotting (FIG. 3) demonstrated that Lys01 is a >10-fold more potent autophagy inhibitor than HCQ or CQ at a concentration of 10 μM. Lys02 and Lys03 produced dose-response relationships for LC3 immunoblotting similar to HCQ or CQ, whereas Lys04, which retains the two chloroquinoline rings present in Lys01, demonstrated intermediate potency in the LC3 autophagy assay To further characterize the effects of Lys01 on autophagy, LN229 GFP-LC3 cells were treated with Lys01 or HCQ (FIG. 4A). Within 4 hours of treatment, in cells treated with HCQ1 μM, punctate fluorescence, indicating an accumulation of ineffective autophagic vesicles, was observed in a minority of cells. HCQ 10 μM produced numerous small puncta, and HCQ 100 μM resulted in larger dense puncta that represent fusion of accumulated autophagic vesicles. Lys01 1 μM produced numerous small puncta, whereas in cells treated with Lys01 10 μM dense puncta similar in appearance to those observed in cells treated with HCQ 100 μM were apparent. All cells treated with Lys01 100 μM were dead by 4 hours. Quantification of the GFP-LC3 puncta per cell demonstrated a significant 5-fold increase in GFP-LC3 puncta between 10 μM Lys01 compared to 10 μM HCQ treatments. The average number of vesicles per cell in cells treated with Lys01 10 μM was higher than in cells treated with 100 μM HCQ (FIG. 4A). Electron micrographs of LN229 GFP-LC3 cells treated with DMSO, HCQ, or Lys01 further characterized the significant morphological difference in the size and number of vesicles produced by blockade of autophagy with these agents (FIG. 4B). Thus, Lys01 produces morphological changes more pronounced than HCQ, a known lysosomal inhibitor, at 10-fold lower concentrations. To determine if Lys01 treatment was inducing production of new autophagic vesicles (an autophagy inducer) or blocking the clearance of autophagy vesicles (an autophagy inhibitor), a bafilomycin clamp experiment was performed (FIG. 4C). LN229 GFP-LC3 cells were treated with DMSO, rapamycin, HCQ 10 μM, and Lys01 10 μM, in the absence or presence of bafilomycin. At 24 hours, rapamycin treatment resulted in a further increase in the LC3II/LC3 ratio in bafilomycin treated cells compared to control cells whereas HCQ- or Lys05-treated cells did not demonstrate an increase in LC3II/LC3I ratio in bafilomycin treated cells compared to control, providing further evidence that Lys01 is an autophagy inhibitor (FIG. 4C).

Figure 4D:
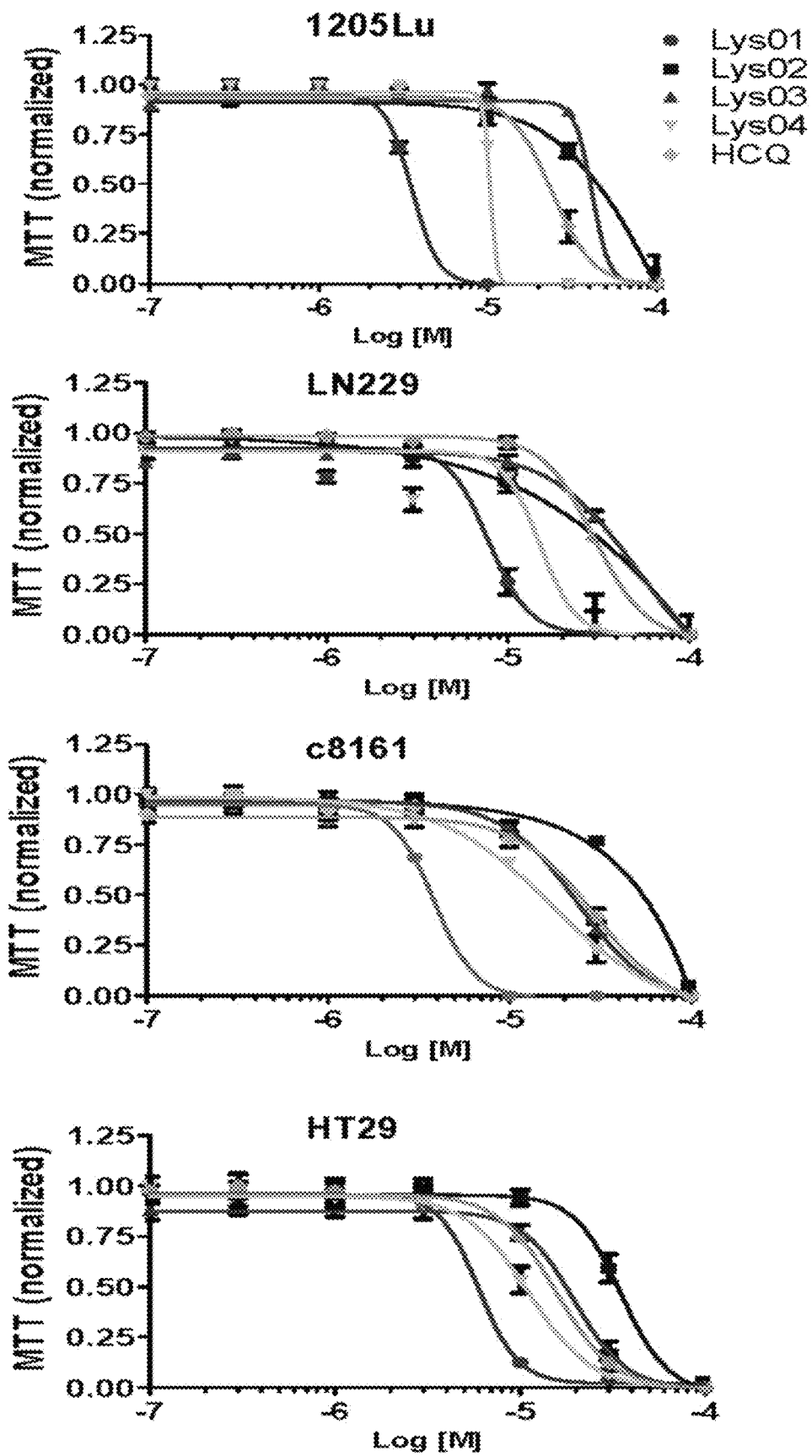

To determine the implications of more potent autophagy inhibition on cytotoxicity, LN229 (glioma), 1205Lu (melanoma), HT-29 (colon) and c8161 (melanoma) cells were treated with Lys01, Lys02, Lys03 Lys04, and HCQ at concentrations between 0.01-100 μM (FIG. 4D). The MTT assay was used to assess viable cells at 72 hours. In the 4 cell lines tested, the IC50 of Lys01 was 4-8 μM (Supplemental Table 2). Near complete cell death after 24 hours was observed in 1205Lu and HCC827 (cell lines which are highly resistant to HCQ) cells treated with 10 μM Lys01. In contrast the IC50 for Lys02, which is a monofunctional CQ derivative (35-91 μM), Lys03, the bisaminoquinoline with methoxy groups replacing chlorine (24-53 μM), or HCQ (15-42 μM) were collectively 9-30-fold less potent than Lys01. Lys04, which retains the bivalent aminoquinoline rings but has an altered linker, had intermediate activity, with IC50 of 10-17 μM. These studies demonstrate that Lys01 is consistently more cytotoxic than other aminoquinolines tested or HCQ. Together with the LC3 western blot data, these results indicate that the most potent cytotoxic autophagy inhibitors contain two aminoquinoline rings, the triamine linker present in Lys01 and a chlorine substituent at the C-7 position of the aminoquinoline ring.

In Vivo Autophagy Inhibition and Antitumor Efficacy Lys05.

Figure 5A:
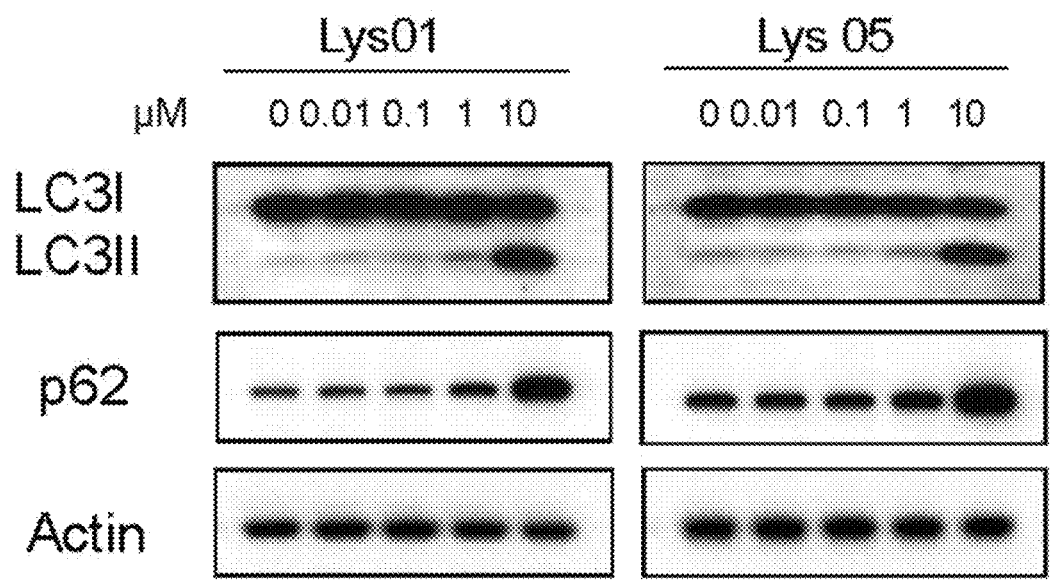
FIGS. 5A, 5B. Autophagy inhibition and cytotoxicity of Lys05, the water soluble salt of Ly01. (5A) Immunoblotting against LC3 and p62 in c8161 cells treated as indicated (5B) MTT assay in c8161 cells at 72 hours. HCQ: Hydroxychloroquine. Values presented are mean+/−SD with 5 replicated per treatment condition*No remaining cells for analysis.
Figure 5B:
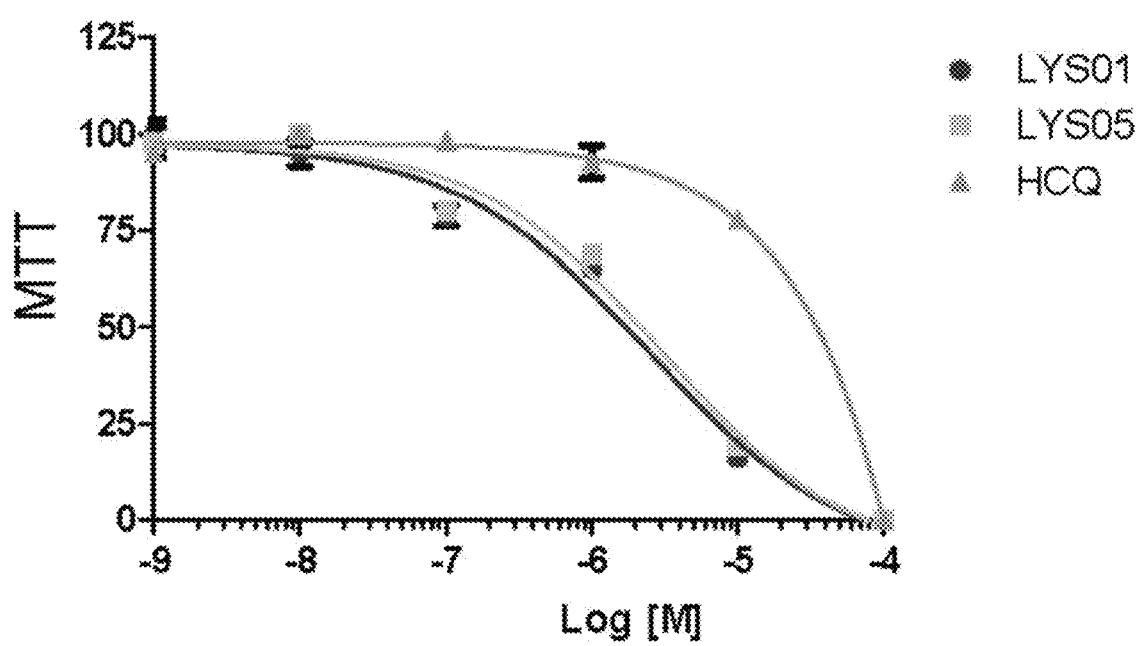
Figure 6A:
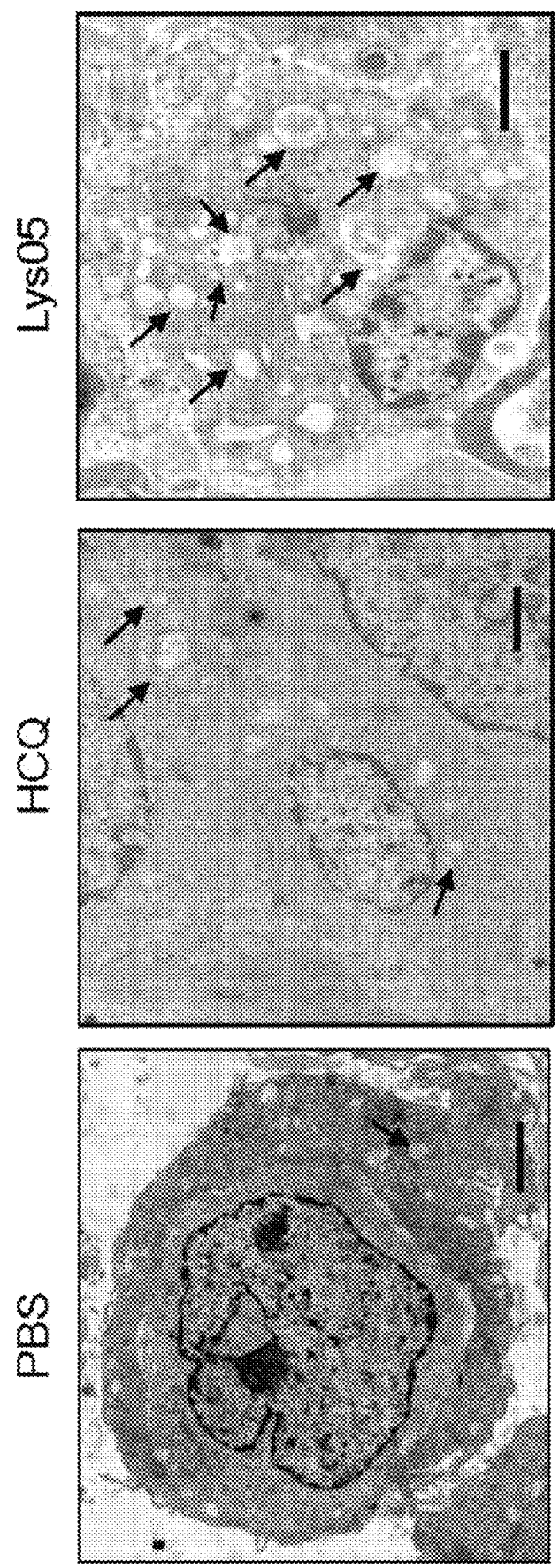
Figure 7A:
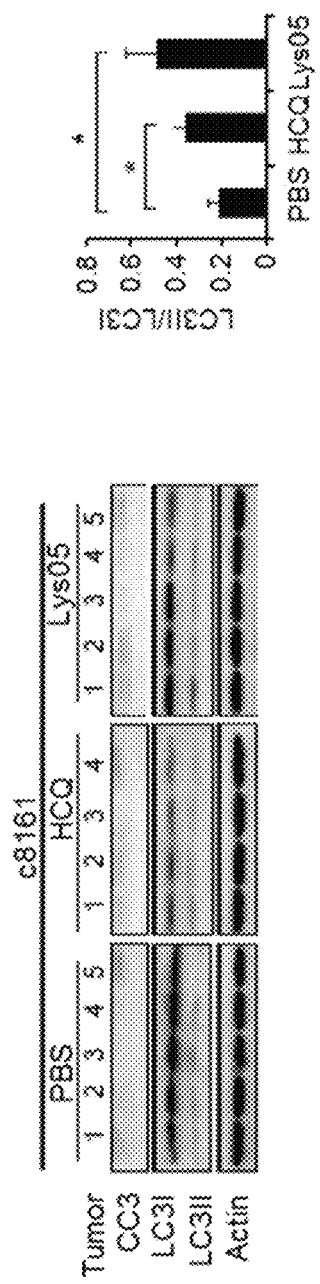

Lys05, the trihydrochloride salt of Lys01 was synthesized to enhance aqueous solubility and to enable in vivo studies. Lys01 and Lys05 produced equivalent dose-dependent increases in the LC3II/LC3I ratio, and accumulation of the autophagy cargo protein p62 (26), and identical IC50 values in the MTT assay, (FIG. 5A, B). To investigate the safety of Lys05 and its in vivo effects on autophagy, c8161 xenografts matched for tumor size were treated with intraperitoneal (i.p.) daily PBS, or equimolar doses of HCQ or Lys05 (HCQ 60 mg/kg (138 nmoles/g), Lys05 76 mg/kg (138 nmoles/g)) for 48 hours. With this high dose, short term treatment no mice died, but after 2 days of dosing, mice treated with Lys05 76 mg/kg i.p. were observed to have arched backs and lethargy. After 48 hours of treatment mice were euthanized, and tumors were processed for electron microscopy (EM). Morphologically, EM demonstrated that cells with intact nuclear and cytoplasmic membranes contained large AV in Lys05-treated tumors (FIG. 6A). Quantification of the mean number of AV/cell in two representative tumor from each treatment group found a significant >2-fold increase in the mean number of AV/cell in Lys05 treated tumors compared to control- or HCQ-treated tumors (FIG. 6B). Significantly higher LC3II/LC3I levels were observed in Lys05-treated tumors compared to control- or HCQ-treated tumors providing further evidence of in vivo autophagy inhibition (FIG. 7A). After 48 hours of treatment, cleaved caspase 3 levels indicative of apoptosis were elevated in Lys05 treated tumors compared to HCQ- or PBS-treated tumors.

Figure 7B:
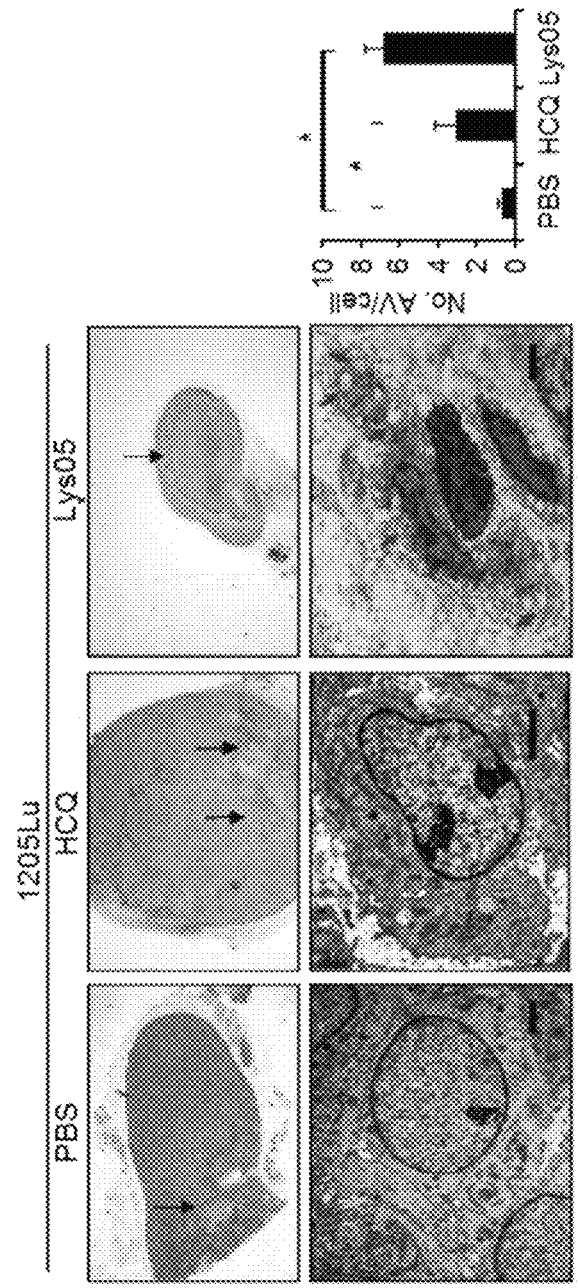

Except for certain models of pancreatic cancer (27), in many animal tumor models, where high levels of autophagy are likely present in untreated tumors (4, 28), treatment with single agent HCQ does not impair tumor growth (29, 30). To determine if a more potent autophagy inhibitor such as Lys05 could significantly impair tumor growth as a single agent 1205Lu xenografts were generated in the flanks of nude mice. For chronic treatment experiments the 1205Lu melanoma model was chosen over the c8161 xenograft model because c8161 xenografts tend to spontaneously ulcerate confounding tumor measurements and safety analysis. Ten mice bearing 1205Lu xenografts were matched for tumor volume per cohort were assigned to either PBS, HCQ 60 mg/kg i.p. or Lys05 76 mg/kg i.p. (equimolar dosing) dosed for 3 days of daily treatment with 2 days off treatment (3/5 days) for all 3 treatment groups, to allow for symptom recovery and to avoid excess toxicity. This schedule was tolerated well for a 14 day period. Tumor growth curves for each of the 3 groups indicated tumor growth was significantly impaired in Lys05 treated tumors compared to controls (FIG. 6C). Lys05 treatment resulted in a 53% reduction in the average daily tumor growth rate compared to vehicle treated controls (31.2 v. 14.6 mm$^3$/day; p=0.002; FIG. 6D). A significant accumulation of AV was observed at the end of 14 days of treatment in both HCQ- and Lys05-treated tumors, but Lys05 treated tumors had a 6-fold increase in AV/cell whereas HCQ-treated tumors had a 3-fold increase in AV/cell compared to control treated tumors (FIG. 7B). Extensive tumor necrosis was observed in the center of Lys05 treated tumors (FIG. 7B).

To determine if lower doses of Lys05 could produce antitumor activity, mice bearing HT-29 colon cancer xenografts were treated with PBS, or Lys05 at 10 mg/kg i.p. daily, 40 mg/kg i.p. daily, or 80 mg/kg i.p. 3/5 days off. Clinical toxicity was observed only in the 80 mg/kg cohort, with 2/8 mice euthanized early for bowel obstruction. Daily dosing for the 10 mg/kg and 40 mg/kg cohorts was well tolerated. The average daily tumor growth rate was significantly impaired in a dose-dependent fashion with Lys05 treatment (FIG. 6E). Tumor growth curves demonstrated that all 3 doses of Lys05 produced significant tumor growth impairment compared to control (FIG. 6F). At the end of the experiment excised tumor weights demonstrated that significant antitumor activity was observed with 10 mg/kg daily dosing (FIG. 6G). Immunoblotting against LC3 in tumor lysates harvested after 14 days of treatment revealed a significant increase in LC3II/LC3I ratio in all Lys05 treated tumors including the 10 mg/kg dosed tumors compared to control (FIG. 7C).

Intestinal Toxicity at the Maximal Administered Dose of Lys05 Resembles a Genetic Autophagy Deficiency.

Figure 8C:
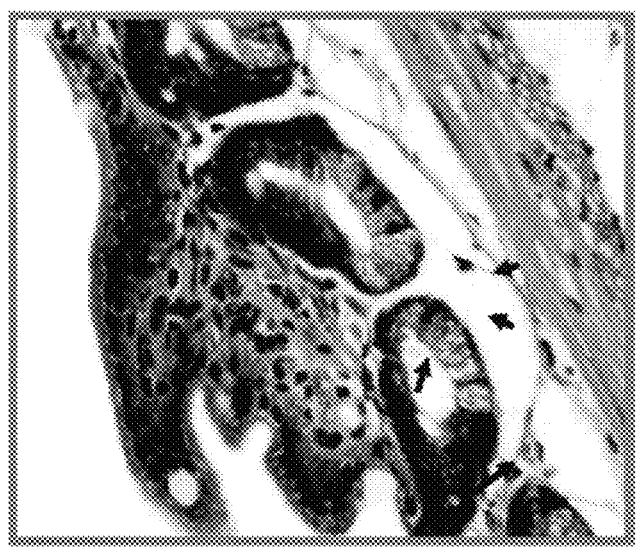
FIGS. 8A, 8B, 8C. Toxicity associated with Lys05 76 mg/kg ip 3/5 days. (8A) Mice were lethargic with arched backs after 3 days of dosing. (8B) 3/10 mice developed bowel obstruction. (8C) Dysmorphic paneth cells (arrows) in the terminal ileum of one mouse.
Figure 8B:
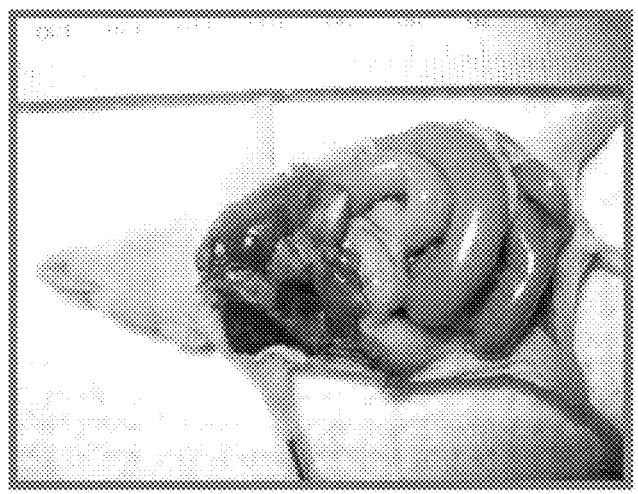
Figure 8A:
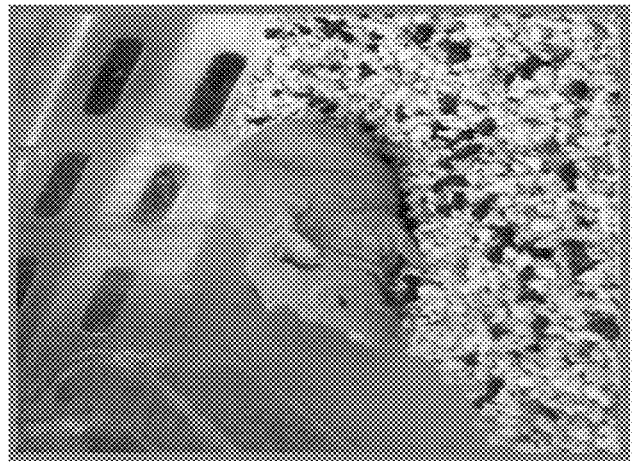

In the 1205lu xenograft experiment, individual animals treated with Lys05 76 mg/kg i.p. 3/5 days appeared lethargic with arched backs (FIG. 8A). Three out of ten mice treated with Lys05 developed signs of bowel obstruction (FIG. 8B). Inspection of the bowel found dilated proximal small intestine with a pseudostricture of the terminal ileum. Histological examination of the ileum revealed no evidence of excess inflammation, fibrosis, or mechanical obstruction, indicating that the obstructive signs observed in the mice were due to pseudo-obstruction or functional ileus. While intestinal villi and crypt architecture were intact, dysmorphic Paneth cells (FIG. 8C) were observed. Paneth cell dysfunction, including reduced size and number of eosinophilic lysozyme-containing granules, has previously been described as the pathognomonic sign of autophagy deficiency in mice and a subset of Crohn's disease patients that have a genetic deficiency in the essential autophagy gene ATG16L1 (31).

In the HT29 dose-finding xenograft experiment there was no significant weight loss observed in any dose cohort (FIG. 9A). Resection of the entire gastrointestinal tract from mice bearing HT-29 tumors after 14 days of treatment demonstrated bowel thickening and obstruction was limited to 80 mg/kg dose cohort (FIG. 9B). Histological examination of the terminal ileum resected from mice bearing HT-29 xenografts treated with PBS ip daily, or Lys05 10 mg/kg ip daily, 40 mg/kg ip daily, and 80 mg/kg ip daily every 3/5 days for 14 days demonstrated dose dependent effects on Paneth cell morphology (FIG. 9C). While the number of Paneth cells/ crypt did not change with treatment (FIG. 9D), the size and number of granules decreased in a dose dependent manner. Scoring on a Paneth cell dysfunction scale (FIG. 10) indicated that Paneth cell dysfunction was observed at all doses tested of Lys05, despite signs and symptoms of toxicity being restricted to the 80 mg/kg dose (FIG. 9E). In mice treated with Lys05 40 mg/kg or 80 mg/kg, but not 10 mg/kg, lysozyme was significantly reduced or absent in Paneth cells (FIG. 9F). Taken together these findings indicate that Lys05-associated Paneth cell dysfunction mimics ATG16L1 deficiency, and lower doses of Lys05 produce significant antitumor activity without dose-limiting toxicity.

Lys05 Inhibits Autophagy by Deacidifying the Lysosome.

Figure 11A:
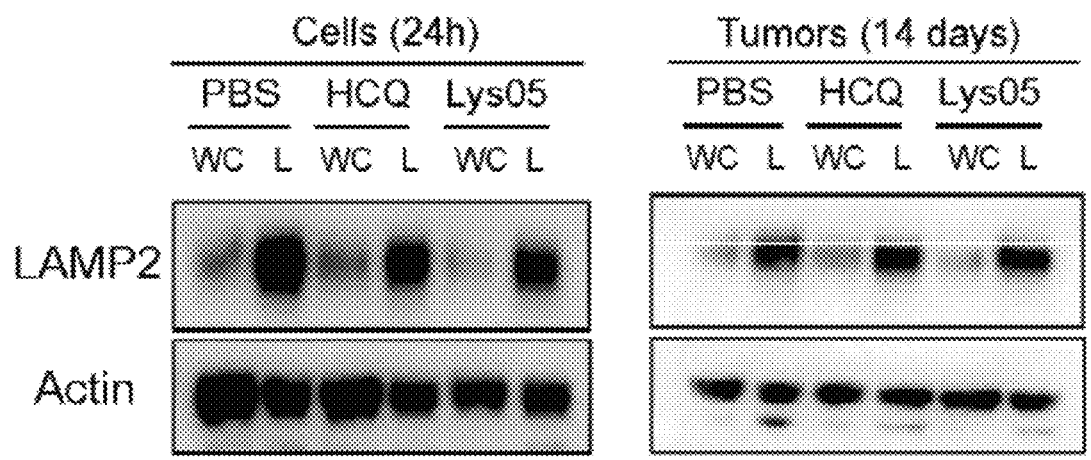
FIGS. 11A, 11B, 11C, 11D. Lys 05 inhibits autophagy by accumulating in and deacidifying the lysosome. (11A) 1205Lu cells (treated with PBS, HCQ 10 μM, or Lys05 10 μM for 24 hours) and harvested 1205 Lu Xenograft tumors (treated with PBS, HCQ 60 mG/kg i.p. 3/5 days, or Lys05 76 mg/kg i.p. 3/5 days for 14 days) were homogenized and fractionated into whole cell (WC) and Lysosomal (L) fractions. LAMP2 immunoblotting confirmed isolation of concentrated lysosomes for analysis. (11B) Concentrations of HCQ or Lys05 in cells and tumor whole cell and lysosomal homogenates. (11C) Fluorescence imaging of 1205Lu cells treated as indicated for 30 minutes and stained with Lysotracker Red. Lysotracker puncta (red) per cell was scored for three high powered fields. Blue: nuclear DAPI staining. Data presented is mean+SEM (11D) Fluorescence imaging of c8161 cells treated as indicated for 24 hours and stained with acridine orange (AO): orange: Aggregated AO, green: diffuse AO FIG. 12. High performance liquid chromatography tandem mass spectrometry assay for HCQ and Lys05. 1205Lu cells (24 hours) and 1205Lu tumors (14 days). WC: Whole cell homogenate L: Lysosomal subfraction HCQ: Hydroxychloroquine FIGS. 13A, 13B, 13C, 13D. Impairment of lysosomal enzymes and extralysosomal leakage associated with Lys05 treatment. (13A) Acid phosphatase activity and (13B) Cathepsin D immunoblotting in whole cell (white, WC) and lysosomal (Black; L) fractions of 1205Lu cells treated with PBC, HCQ 10 μM, Lys05 10 μM for 24 hours. Graphs show the mean+/−SEM for three independent experiments. (13C) Acid phosphatase activity and (13D) Cathepsin D immuno-blotting in whole cell (white, WC) and lysosomal (Black; L) fractions of 1205 Lu xenografts treated with PBS. HCQ 60 mg/kg, Lys05 76 mg/kg i.p. 3/5 days (tumors). Whole cell homogenates (white) and lysosomal homogenates (black) were prepared from three separate tumors were pooled together. *p<0.05.
Figure 11B:
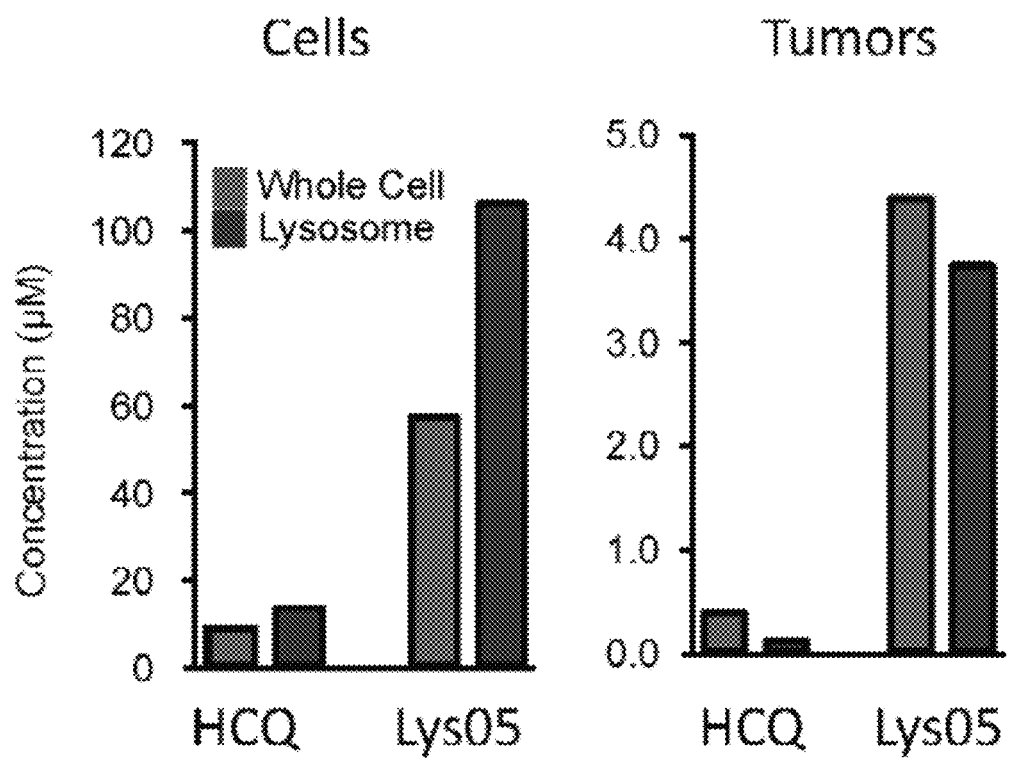
Figure 12:
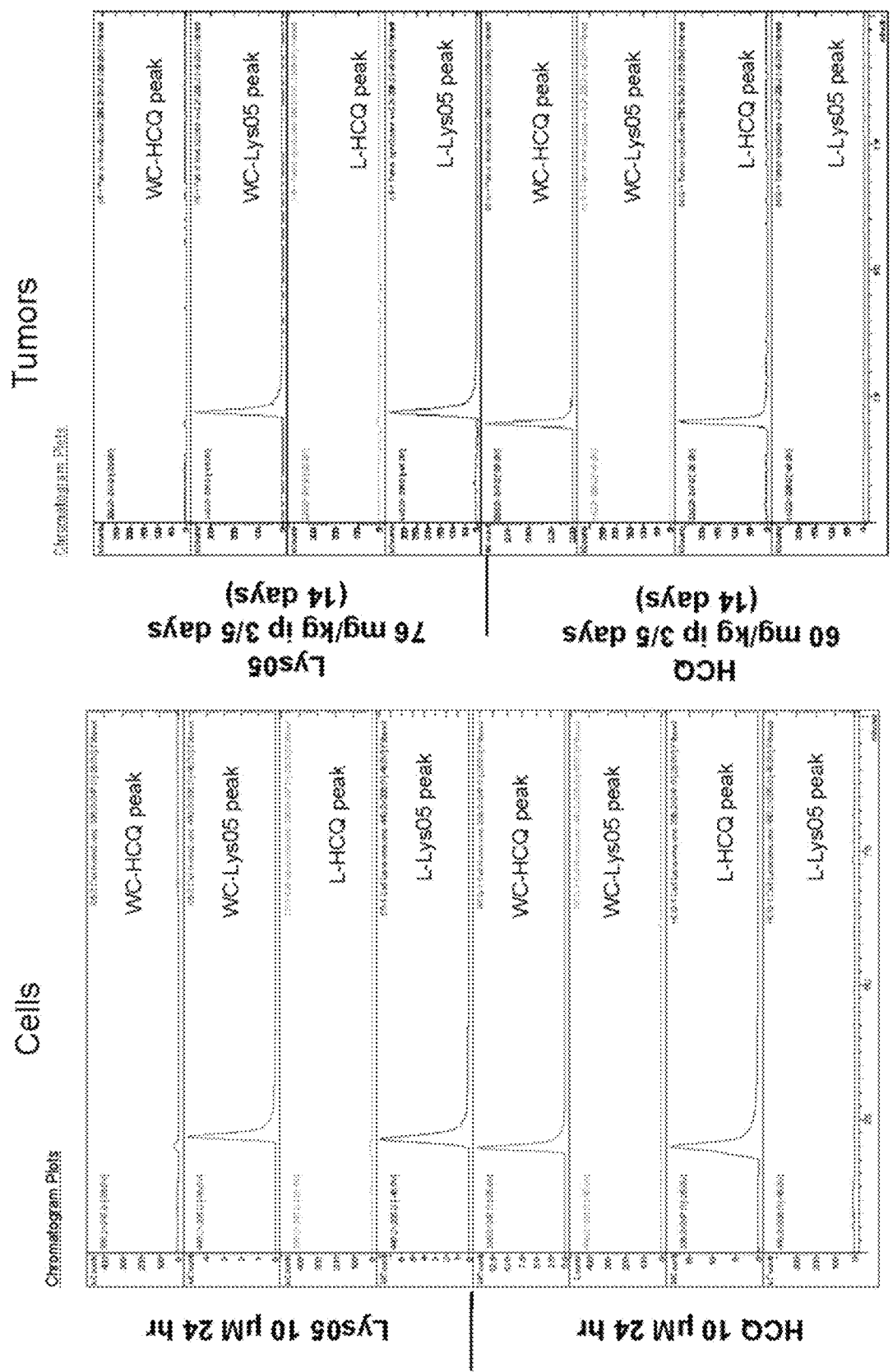

To compare the relative lysosomal accumulation of Lys05 compared to HCQ, lysosomes were subfractionated from 1205Lu cells treated with PBS, HCQ 10 µM, or Lys05 10 µM, and 1205Lu tumors harvested after 14 days of treatment with PBS, HCQ 60 mg/kg i.p., or Lys05 76 mg./kg i.p. every 3/5 days. Immunoblotting against the lysosomal marker LAMP2 confirmed adequate separation of the lysosomal and whole cell population in both cells and tumor samples (FIG. 11A). HPLC tandem mass spectrometry (MS/MS) measurements (FIG. 12) determined that the concentrations of Lys05 and HCQ in the whole cell homogenate treated with Lys05 10 µM or HCQ 10 µM for 24 hours were 57 µM and 8 µM respectively, indicating an 6-fold higher concentration of Lys05 within the cell compared to HCQ. The concentration of Lys05 and HCQ in the lysosomal fraction of cells treated with Lys05 10 µM or HCQ 10 µM were 105 µM and 13 µM respectively, indicating an 8-fold higher concentration of Lys05 in the lysosome compared to HCQ. This difference in cellular and lysosomal accumulation of Lys05 and HCQ was more marked in tumor tissue. There was an 11-fold higher concentration and a 34-fold higher concentration of Lys05 compared to HCQ in whole cell homogenates and lysosomes, respectively, within tumors (FIG. 11B).

Figure 11C:
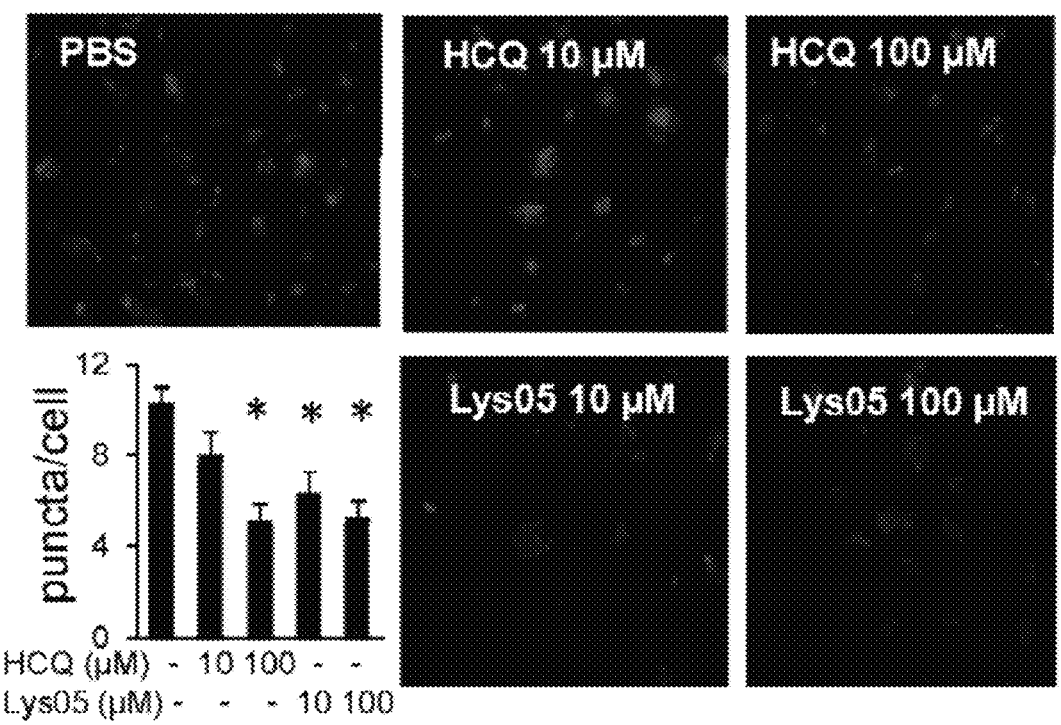
Figure 11D:
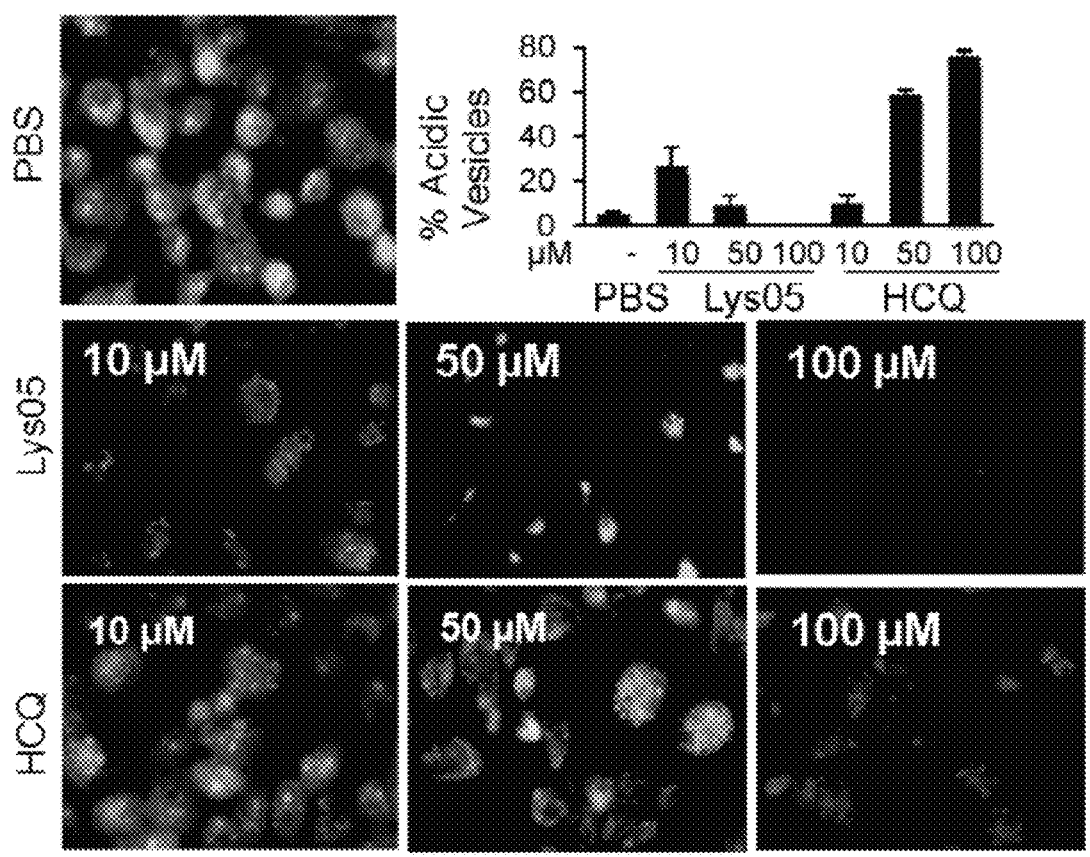

Having established that Lys05 more effectively accumulates in the lysosome than HCQ, the functional effects of this accumulation were investigated. 1205Lu cells were treated with vehicle, Lys05 and HCQ, and stained the Lysotracker Red (FIG. 11C). Within 30 minutes of treatment, fewer Lysotracker-positive puncta were observed in Lys05 treated cells at both 10 µM and 100 µM concentrations. In contrast, a significant decrease in Lysotracker positive puncta was observed in cells treated with HCQ 100 µM, but not observed in cells treated with HCQ 10 µM. To understand the implications of this more potent and complete lysosomal inhibition, 1205Lu cells were treated with vehicle, Lys05, or HCQ and stained with acridine orange (AO; a dye which aggregates in all endovesicular acidic compartments) at 24 hours (FIG. 11D). HCQ produced a dose-dependent accumulation of acidic vesicles. In contrast, Lys05 caused an accumulation of acidic vesicles at lower doses (10 µM), but at higher doses (50 µM), no acidic vesicles were observed, indicating the complete deacidification of the endovesicular system.

Figure 13B:
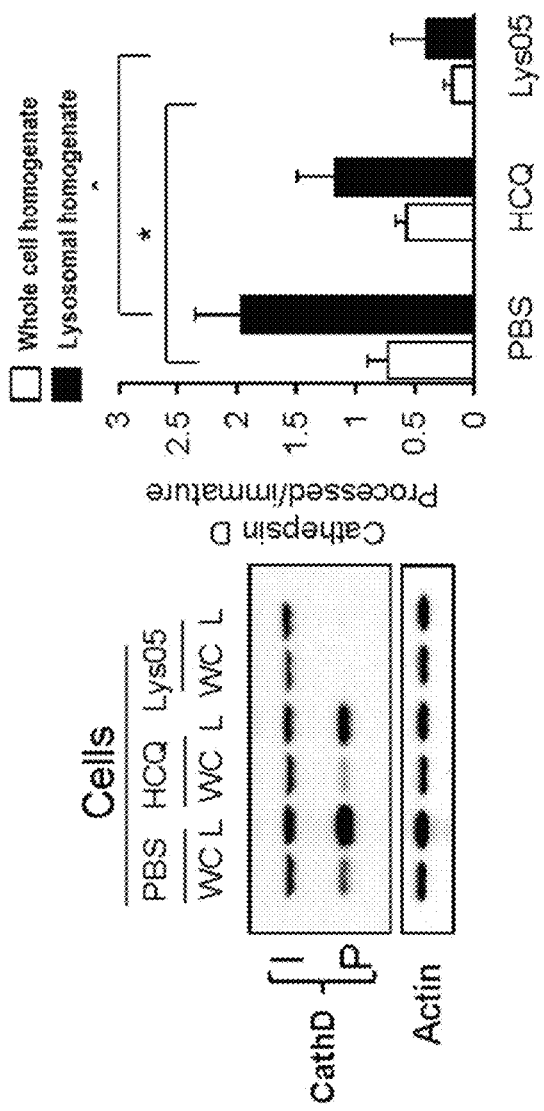
Figure 13A:
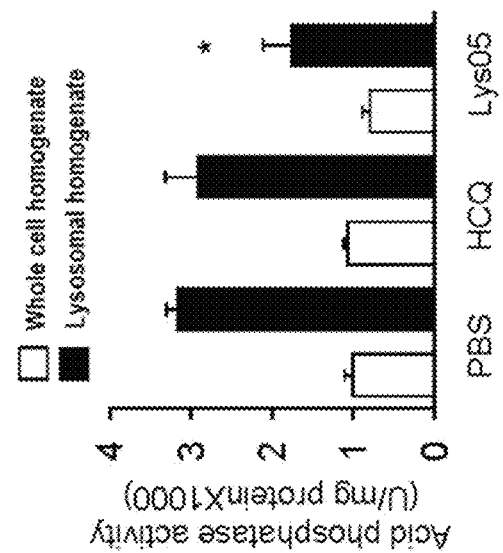

Finally, the functional consequences of lysosomal deacidification were investigated by measuring enzymatic activity of acid phosphatase. In 1205Lu cells treated with PBS, HCQ 10 µM or Lys05 10 µM, within 24 hours there is a 43% reduction in acid phosphatase activity in the lysosomal fraction of Lys05 treated versus PBS treated cells (FIG. 13A). Leakage of certain lysosomal enzymes such as activated cathepsins, could lead to an autophagy-independent cell death Within 24 hours of treatment of 1205Lu cells with PBS, HCQ or Lys05, there is decreased acid-dependent processing of immature cathepsin D to the mature activated form within the lysosome in Lys05-treated compared to HCQ- or PBS-treated cells (FIG. 13B), In 1205Lu xenograft tumors, after 14 days of treatment there was a 1.75-fold increase in extralysosomal acid phosphatase activity in the Lys05-treated tumors, suggesting that chronic treatment can lead to extralysosomal leakage of enzymes (FIG. 13C), but increased acid-dependent processing of cathepsin D within the whole cell homogenate was not observed in Lys05 treated tumors (FIG. 13D). These results indicate that high doses of Lys05 cause lysosomal dysfunction by deacidifying the lysosome, leading to impairment of lysosomal enzymes, and effective autophagy inhibition, whereas high doses of HCQ incompletely deacidify the lysosome, leading to incomplete autophagy inhibition associated with less cell death.

Additional compounds Lys06-Lys18

Additional Lys01 derivatives have been synthesized and tested (FIG. 14, FIG. 15A). In 72 hour MTT assays the IC50's of compounds Lys01-Lys13 demonstrate increased or decreased activity compared to HCQ and CQ (Table 1, FIG. 16). In most cases the Lys01 derivatives are more active than CQ or HCQ. These findings further refine the starting point for further drug development of Lys01 derivatives.

Activity of Lys01 Derivatives in Malaria.

Table 2, FIG. 17 shows the IC50 values for Lys01 derivative-induced cell death in the human cancer cell LN229 and a number of strains of *P. Falciparum* grown in invitro in human RBC. There is a similar activity profile for anticancer activity of Lys01 derivatives and malaria cytotoxicity. Lys01 was more active than artesunate in some CQ-resistant cell lines.

CONCLUSIONS

Potential Commercial Uses and Applications: Lys01 and Lys05 are lead compounds with great potential to be optimized further for potency as a novel autophagy inhibitor. Autophagy inhibition is a new therapeutic strategy in cancer that is applicable to every cancer. There are currently over 30 HCQ trials in cancer patients involving nearly every tumor type. Due to its low potency and poor pharmacology, in humans HCQ will likely not yield the promising augmentation of anticancer therapy observed in laboratory models. An optimized derivative of Lys01 could be developed as a second generation autophagy inhibitor. The GI toxicity associated with Paneth cell dysfunction observed at LD30 doses of Lys05, support the mechanism of action of the drug, and also suggests that colon cancers, which often share features with Paneth cells, may be a tumor type that may be especially sensitive to Lys05 and its optimized derivatives. Additional cancers worth investigating include melanoma, and non small cell lung cancer, since melanoma cell lines demonstrated the highest difference in sensitivity to Lys01 compared to HCQ, and an EGFR mutated lung cancer cell line demonstrated sensitivity to both HCQ and Lys05. The synthesis of Lys01 was designed such that there is no overlap with other patented and/or published aminoquinoline compounds. Further mechanistic studies are planned that are to identify pharmacodynamics assays that guide drug development. Pharmacokinetic studies planned in mice establish initial in vivo profile.

Other similar technologies and competing products: Novel chloroquine derivatives for use as anticancer agents is an active area of investigation (16). Autophagy has been identified as one of the top ten areas of research in which the NIH will invest in the next few years. No studies to date have leveraged the potential of bivalency as the inventors provide here. In addition, most studies lack the in vivo studies and the mechanistic studies herein reported that can guide further development of optimize lead compounds for drug development.

Advantages over other similar technologies and products: Thus, the present application has shows that the disclosed series of bisaminoquinolines are potent autophagy inhibitors that have single agent antitumor activity in an in vivo tumor model.

REFERENCES

1. Lun J J, DeBerardinis R J, Thompson C B. Autophagy in metazoans: cell survival in the land of plenty. Nat Rev Mol Cell Biol 2005; 6: 439-48.
2. Amaravadi R K, Thompson C B. The roles of therapy-induced autophagy and necrosis in cancer treatment. Clin Cancer Res 2007; 13: 7271-9.
3. Amaravadi R K, Yu D, Lum J J, et al. Autophagy inhibition enhances therapy-induced apoptosis in a Myc-induced model of lymphoma. J Clin Invest 2007; 117: 326-36.
4. Degenhardt K, Mathew R, Beaudoin B, et al. Autophagy promotes tumor cell survival and restricts necrosis, inflammation, and tumorigenesis. Cancer Cell 2006; 10: 51-64.
5. Amaravadi R K. Autophagy-induced tumor dormancy in ovarian cancer. J Clin Invest 2008.
6. Carew J S, Nawrocki S T, Kahue C N, et al. Targeting autophagy augments the anticancer activity of the histone deacetylase inhibitor SAHA to overcome Bcr-Abl-mediated drug resistance. Blood 2007.
7. Degtyarev M, De Maziere A, Orr C, et al. Akt inhibition promotes autophagy and sensitizes PTEN-null tumors to lysosomotropic agents. J Cell Biol 2008; 183: 101-16.
8. Sotelo J, Briceno E, Lopez-Gonzalez M A. Adding chloroquine to conventional treatment for glioblastoma multiforme: a randomized, double-blind, placebo-controlled trial. Ann Intern Med 2006; 144: 337-43.
9. Amaravadi R K, Lippincott-Schwartz J, Yin X M, et al. Principles and Current Strategies for Targeting Autophagy for Cancer Treatment. Clin Cancer Res 2011; 17: 654-66.
10. Rosenfeld M R G S, Brem S, Mikkelson T, Wang D, Piao S, Davis L, O'Dwyer P J, Amaravadi R K Pharmacokinetic analysis and pharmacodynamic evidence of autophagy inhibition in patients with newly diagnosed glioblastoma treated on a phase I trial of hydroxychloroquine in combination with adjuvant temozolomide and radiation (ABTC 0603). J Clin Oncol 2010; 28: Abstract #3086.
11. Vance D, Shah M, Joshi A, Kane R S. Polyvalency: a promising strategy for drug design. Biotechnol Bioeng 2008; 101: 429-34.
12. Shrivastava A, Nunn A D, Tweedle M F. Designer peptides: learning from nature. Curr Pharm Des 2009; 15: 675-81.
13. Girault S, Grellier P, Berecibar A, et al. Antiplasmodial activity and cytotoxicity of bis-, tris-, and tetraquinolines with linear or cyclic amino linkers. J Med Chem 2001; 44: 1658-65.
14. Vennerstrom J L, Ager A L, Jr., Dorn A, et al. Bisquinolines. 2. Antimalarial N,N-bis(7-chloroqutinolin-4-yl) heteroalkanediamines. J Med Chem 1998; 41: 4360-4.
15. Burnett J C, Schmidt J J, Stafford R G, et al. Novel small molecule inhibitors of botulinum neurotoxin A metalloprotease activity. Biochem Biophys Res Commun 2003; 310: 84-93.
16. Hu C, Raja Solomon V, Cano P, Lee H. A 4-aminoquinoline derivative that markedly sensitizes tumor cell killing by Akt inhibitors with a minimum cytotoxicity to non-cancer cells. Eur J Med Chem 2010; 45: 705-9.
17. Solomon V R, Hu C, Lee H. Design and synthesis of chloroquine analogs with anti-breast cancer property. Eur J Med Chem 2010; 45: 3916-23.
18. T. Higuchi H O, M. Umezawa, H. Kim, Y. Wataya. Compound with Antimalarial Activity and Antimalarial Drug Containing the Same as Active Ingredient. WO/2007/097450.
19. Lee W W, Berridge B J, Jr., Ross L O, Goodman L. Synthesis of Mustards from Putrescine, Cadaverine, and 1,3-Diaminopropane. J Med Chem 1963; 6: 567-9.
20. Kaschula C H, Egan T J, Hunter R, et al. Structure-activity relationships in 4-aminoquinoline antiplasmodials. The role of the group at the 7-position. J Med Chem 2002; 45: 3531-9.

21. Adams A, Jarrott B, Elmes B C, Denny W A, Wakelin L P. Interaction of DNA-intercalating antitumor agents with adrenoceptors. Mol Pharmacol 1985; 27: 480-91.
22. Gourdie T A, Valu K K, Gravatt G L, et al. DNA-directed alkylating agents. 1. Structure-activity relationships for acridine-linked aniline mustards: consequences of varying the reactivity of the mustard. J Med Chem 1990; 33: 1177-86.
23. Bailey D M, DeGrazia C G, Hoff S J, et al. Bispyridinamines: a new class of topical antimicrobial agents as inhibitors of dental plaque. J Med Chem 1984; 27: 1457-64.
24. Vicker N, Burgess L, Chuckowree I S, et al. Novel angular benzophenazines: dual topoisomerase I and topoisomerase II inhibitors as potential anticancer agents. J Med Chem 2002; 45: 721-39.
25. Tanida I, Ueno T, Kominami E. LC3 conjugation system in mammalian autophagy. Int J Biochem Cell Biol 2004; 36: 2503-18.
26. Pankiv S, Clausen T H, Lamark T, et al. p62/SQSTM1 binds directly to Atg8/LC3 to facilitate degradation of ubiquitinated protein aggregates by autophagy. J Biol Chem 2007; 282: 24131-45.
27. Yang S, Wang X, Contino G, et al. Pancreatic cancers require autophagy for tumor growth. Genes Dev 2011; 25: 717-29.
28. Ma X, Piao S, Wang D W, et al. Measurements of tumor cell autophagy predict invasiveness, resistance to chemotherapy, and survival in melanoma. Clin Cancer Res 2011.
29. Fan Q W, Cheng C, Hackett C, et al. Akt and autophagy cooperate to promote survival of drug-resistant glioma. Sci Signal 2010; 3: ra81.
30. Saleem A, Dvorzhinski D, Santanam U, et al. Effect of dual inhibition of apoptosis and autophagy in prostate cancer. Prostate 2012.
31. Cadwell K, Liu J Y, Brown S L, et al. A key role for autophagy and the autophagy gene Atg16l1 in mouse and human intestinal Paneth cells. Nature 2008; 456: 259-63.

The invention claimed is:

1. A compound of formula I

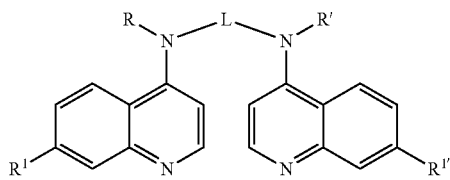

wherein
$R^1$ is H, F, Cl, Br, I, CN, $NO_2$, $C_1$-$C_6$ alkyl, $C_1$-$C_6$ alkyl substituted with 1 or 2 hydroxyl groups, $C_1$-$C_6$ alkyl substituted with 3-5 fluoro groups, O—$C_1$-$C_6$ alkyl, O—$C_1$-$C_6$ alkyl substituted with $OCH_3$, $C_2$-$C_7$ acyl, or $C_2$-$C_7$ ester;
$R^{1'}$ is H, F, Br, I, CN, $NO_2$, $C_1$-$C_6$ alkyl, $C_1$-$C_6$ alkyl substituted with 1 or 2 hydroxyl groups, $C_1$-$C_6$ alkyl substituted with 3-5 fluoro groups, O—$C_1$-$C_6$ alkyl, O—$C_1$-$C_6$ alkyl substituted with $OCH_3$, $C_2$-$C_7$ acyl, or $C_2$-$C_7$ ester;
R and R' are each independently H;
L is a

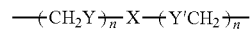

group;
X is N—R";
Y is absent;
Y' is absent;
R" is a $C_1$-$C_6$ alkyl group; and
n is 4;
or a pharmaceutically acceptable salt, enantiomer, diastereomer, solvate or polymorph thereof.

2. A pharmaceutical composition comprising an effective amount of at least one compound according to claim 1 in combination with a pharmaceutically acceptable carrier, additive or excipient or in combination with at least one additional anticancer agent.

3. The compound of claim 1, wherein $R^1$ and $R^{1'}$ are each H.

4. The compound of claim 1, wherein $R^1$ and $R^{1'}$ are each F.

5. The compound of claim 1, wherein $R^1$ and $R^{1'}$ are each $C_1$-$C_6$ alkyl.

6. The compound of claim 1, wherein $R^1$ and $R^{1'}$ are each $C_1$-$C_6$ alkyl substituted with 1 or 2 hydroxyl groups, $C_1$-$C_6$ alkyl substituted with 3-5 fluoro groups.

7. The compound of claim 1, wherein $R^1$ and $R^{1'}$ are each O—$C_1$-$C_6$ alkyl.

8. The compound of claim 1, wherein $R^1$ and $R^{1'}$ are each O—$C_1$-$C_6$ alkyl substituted with $OCH_3$.

9. The compound of claim 1, wherein $R^1$ and $R^{1'}$ are each acetyl.

10. The compound of claim 1, wherein $R^1$ and $R^{1'}$ are each oxycarbonyl ester or carboxyester.

11. The compound of claim 1, wherein R" is a $C_1$ alkyl group.

12. The compound of claim 1, wherein $R^1$ is F, Cl, or Br and $R^{1'}$ is F or Br.

13. The compound of claim 1, wherein $R^1$ is Cl and $R^{1'}$ is F.

14. The compound of claim 12, wherein R" is $CH_3$.

15. The compound of claim 13, wherein R" is $CH_3$.

* * * * *